US008337457B2

(12) United States Patent
Booma et al.

(10) Patent No.: US 8,337,457 B2
(45) Date of Patent: Dec. 25, 2012

(54) SYSTEMS AND METHODS FOR DELIVERING A THERAPEUTIC AGENT

(75) Inventors: Glenn R. Booma, Natick, MA (US); Alessandro Pizzochero, Chelmsford, MA (US); J. Richard Gyory, Sudbury, MA (US)

(73) Assignee: SpringLeaf Therapeutics, Inc., Boston, MA (US)

( * ) Notice: Subject to any disclaimer, the term of this patent is extended or adjusted under 35 U.S.C. 154(b) by 0 days.

(21) Appl. No.: 13/101,749

(22) Filed: May 5, 2011

(65) Prior Publication Data

US 2011/0275997 A1 Nov. 10, 2011

Related U.S. Application Data

(60) Provisional application No. 61/331,763, filed on May 5, 2010.

(51) Int. Cl.
*A61M 37/00* (2006.01)
(52) U.S. Cl. .......................... 604/132; 604/133; 604/153
(58) Field of Classification Search .............. 604/63–67, 604/93.01, 131–156, 174, 191, 263, 503, 604/890.1
See application file for complete search history.

(56) References Cited

U.S. PATENT DOCUMENTS

| | | | |
|---|---|---|---|
| 3,573,511 A | 4/1971 | Noren | |
| 4,060,741 A | 11/1977 | Schafft | |
| 4,093,885 A | 6/1978 | Brown | |
| 4,194,062 A | 3/1980 | Carides et al. | |
| 4,382,882 A | 5/1983 | Vogel et al. | |
| 4,648,271 A | 3/1987 | Woolf | |
| 5,016,047 A | 5/1991 | Meacham | |
| 5,255,809 A | 10/1993 | Ervin et al. | |
| 5,268,082 A | 12/1993 | Oguro et al. | |
| 5,351,164 A | 9/1994 | Grigortchak et al. | |
| 5,432,395 A | 7/1995 | Grahn | |
| 5,460,904 A | 10/1995 | Gozdz et al. | |
| 5,478,668 A | 12/1995 | Gozdz et al. | |

(Continued)

FOREIGN PATENT DOCUMENTS

DE 19809483 9/1999

(Continued)

OTHER PUBLICATIONS

Biovalue Products, e-Patch, Jun. 26, 2006, http://www.valeritas.com/epatch.shtml.

(Continued)

*Primary Examiner* — Nicholas Lucchesi
*Assistant Examiner* — Gerald Landry, II
(74) *Attorney, Agent, or Firm* — Cooley LLP

(57) ABSTRACT

In one embodiment, an apparatus comprises a reservoir for containing a fluid, a first actuator, a transfer structure, and a second actuator. The first actuator is configured to exert a first force on the reservoir when moved from a first configuration to a second configuration such that a first volume of fluid within the reservoir is communicated out of the reservoir. The transfer structure is disposed between the first actuator and the reservoir and has a surface configured to engage the reservoir such that the first force exerted by the first actuator is distributed across a surface of the reservoir engaged by the transfer structure. The second actuator is configured to exert a second force on the reservoir when the second actuator is moved from a first configuration to a second configuration such that a second volume of fluid within the reservoir is communicated out of the fluid reservoir.

29 Claims, 18 Drawing Sheets

U.S. PATENT DOCUMENTS

| | | | |
|---|---|---|---|
| 5,567,284 A | 10/1996 | Bauer et al. | |
| 5,671,905 A * | 9/1997 | Hopkins, Jr. | 251/129.01 |
| 5,747,915 A | 5/1998 | Benavides | |
| 5,770,913 A | 6/1998 | Mizzi | |
| 5,800,420 A | 9/1998 | Gross et al. | |
| 5,848,911 A | 12/1998 | Garcin | |
| 5,848,991 A | 12/1998 | Gross et al. | |
| 5,858,001 A | 1/1999 | Tsals et al. | |
| 5,866,971 A | 2/1999 | Lazarus et al. | |
| 5,907,211 A | 5/1999 | Hall et al. | |
| 5,954,079 A | 9/1999 | Barth et al. | |
| 5,957,895 A | 9/1999 | Sage et al. | |
| 5,986,864 A | 11/1999 | Davis | |
| 5,989,423 A | 11/1999 | Kamen et al. | |
| 6,098,661 A | 8/2000 | Yim et al. | |
| 6,109,852 A | 8/2000 | Shahinpoor et al. | |
| 6,400,489 B1 | 6/2002 | Suzuki et al. | |
| 6,416,495 B1 * | 7/2002 | Kriesel et al. | 604/132 |
| 6,517,972 B1 | 2/2003 | Amatucci | |
| 6,530,900 B1 | 3/2003 | Daily et al. | |
| 6,545,384 B1 | 4/2003 | Pelrine et al. | |
| 6,555,945 B1 | 4/2003 | Baughman et al. | |
| 6,577,039 B2 | 6/2003 | Ishida et al. | |
| 6,586,810 B2 | 7/2003 | Thakur | |
| 6,589,229 B1 | 7/2003 | Connelly et al. | |
| 6,599,662 B1 | 7/2003 | Chiang et al. | |
| 6,682,500 B2 | 1/2004 | Soltanpour et al. | |
| 6,687,536 B1 | 2/2004 | Beck et al. | |
| 6,689,100 B2 | 2/2004 | Connelly et al. | |
| 6,699,218 B2 | 3/2004 | Flaherty et al. | |
| 6,752,787 B1 | 6/2004 | Causey, III et al. | |
| 6,828,062 B2 | 12/2004 | Lu et al. | |
| 6,938,945 B2 | 9/2005 | Wald et al. | |
| 6,960,192 B1 | 11/2005 | Flaherty et al. | |
| 6,982,514 B1 | 1/2006 | Lu et al. | |
| 7,005,078 B2 | 2/2006 | Van Lintel et al. | |
| 7,014,625 B2 | 3/2006 | Bengtsson | |
| 7,025,743 B2 | 4/2006 | Mann et al. | |
| 7,044,928 B2 | 5/2006 | LeMay et al. | |
| 7,115,108 B2 | 10/2006 | Wilkinson et al. | |
| 7,144,384 B2 | 12/2006 | Gorman et al. | |
| 7,156,838 B2 | 1/2007 | Gabel et al. | |
| 7,205,699 B1 | 4/2007 | Liu et al. | |
| 7,273,889 B2 | 9/2007 | Memelstein et al. | |
| 7,274,128 B1 | 9/2007 | Liu et al. | |
| 7,298,017 B1 | 11/2007 | Liu et al. | |
| 7,364,568 B2 | 4/2008 | Angel et al. | |
| 7,410,476 B2 | 8/2008 | Wilkinson et al. | |
| 7,435,362 B2 | 10/2008 | Muraoka et al. | |
| 7,444,812 B2 | 11/2008 | Kirkpatrick et al. | |
| 7,449,090 B2 | 11/2008 | Andrews et al. | |
| 7,541,715 B2 | 6/2009 | Chiang et al. | |
| 7,569,050 B2 | 8/2009 | Moberg et al. | |
| D602,155 S | 10/2009 | Foley et al. | |
| D602,586 S | 10/2009 | Foley et al. | |
| 7,632,247 B2 | 12/2009 | Adams | |
| 7,652,907 B2 | 1/2010 | Bloch et al. | |
| 7,678,079 B2 | 3/2010 | Shermer et al. | |
| 7,733,000 B2 | 6/2010 | Kudoh | |
| 7,828,771 B2 | 11/2010 | Chiang et al. | |
| 7,829,213 B2 | 11/2010 | Jacobson et al. | |
| 7,872,396 B2 | 1/2011 | Chiang et al. | |
| 7,923,895 B2 | 4/2011 | Chiang et al. | |
| 7,994,686 B2 | 8/2011 | Chiang et al. | |
| 7,999,435 B2 | 8/2011 | Chiang et al. | |
| 2001/0053887 A1 | 12/2001 | Douglas et al. | |
| 2002/0039620 A1 | 4/2002 | Shahinpoor et al. | |
| 2003/0135159 A1 | 7/2003 | Daily et al. | |
| 2003/0167035 A1 | 9/2003 | Flaherty et al. | |
| 2003/0170166 A1 | 9/2003 | Smalley et al. | |
| 2004/0038251 A1 | 2/2004 | Smalley et al. | |
| 2005/0112427 A1 | 5/2005 | Bailey et al. | |
| 2005/0119618 A1 | 6/2005 | Gonnelli | |
| 2005/0171477 A1 * | 8/2005 | Rubin et al. | 604/156 |
| 2005/0227071 A1 | 10/2005 | Muraoka et al. | |
| 2006/0095014 A1 | 5/2006 | Ethelfield | |
| 2006/0102455 A1 | 5/2006 | Chiang et al. | |
| 2006/0169954 A1 | 8/2006 | Smela et al. | |
| 2006/0206099 A1 | 9/2006 | Olsen | |
| 2006/0231399 A1 | 10/2006 | Smalley et al. | |
| 2007/0021733 A1 | 1/2007 | Hansen et al. | |
| 2007/0049865 A1 | 3/2007 | Radmer et al. | |
| 2007/0112301 A1 | 5/2007 | Preuthun et al. | |
| 2007/0112328 A1 * | 5/2007 | Steinbach et al. | 604/500 |
| 2007/0282269 A1 | 12/2007 | Carter et al. | |
| 2007/0287753 A1 | 12/2007 | Charney et al. | |
| 2007/0299397 A1 | 12/2007 | Alferness et al. | |
| 2007/0299398 A1 | 12/2007 | Alferness et al. | |
| 2007/0299399 A1 | 12/2007 | Alferness et al. | |
| 2007/0299400 A1 | 12/2007 | Alferness et al. | |
| 2007/0299401 A1 | 12/2007 | Alferness et al. | |
| 2007/0299408 A1 | 12/2007 | Alferness et al. | |
| 2008/0009805 A1 | 1/2008 | Ethelfield | |
| 2008/0015494 A1 | 1/2008 | Santini, Jr. et al. | |
| 2008/0051710 A1 | 2/2008 | Moberg et al. | |
| 2008/0058718 A1 | 3/2008 | Adams et al. | |
| 2008/0157713 A1 | 7/2008 | Chiang et al. | |
| 2008/0160373 A1 | 7/2008 | Schumm | |
| 2008/0167620 A1 | 7/2008 | Adams et al. | |
| 2008/0215006 A1 | 9/2008 | Thorkild | |
| 2008/0249468 A1 * | 10/2008 | Edwards et al. | 604/140 |
| 2008/0255516 A1 | 10/2008 | Yodfat et al. | |
| 2008/0257718 A1 | 10/2008 | Chiang et al. | |
| 2008/0269687 A1 | 10/2008 | Chong et al. | |
| 2008/0281270 A1 | 11/2008 | Cross et al. | |
| 2008/0317615 A1 | 12/2008 | Banister | |
| 2008/0319392 A1 * | 12/2008 | Angel et al. | 604/151 |
| 2008/0319414 A1 | 12/2008 | Yodfat et al. | |
| 2009/0014320 A1 | 1/2009 | Chiang et al. | |
| 2009/0028824 A1 * | 1/2009 | Chiang et al. | 424/85.7 |
| 2009/0036867 A1 | 2/2009 | Glejboel et al. | |
| 2009/0054866 A1 | 2/2009 | Teisen-Simony et al. | |
| 2009/0062747 A1 | 3/2009 | Saul | |
| 2009/0088693 A1 | 4/2009 | Carter | |
| 2009/0088694 A1 | 4/2009 | Carter et al. | |
| 2009/0088722 A1 | 4/2009 | Wojcik | |
| 2009/0099521 A1 | 4/2009 | Gravesen et al. | |
| 2009/0099522 A1 | 4/2009 | Kamen et al. | |
| 2009/0124997 A1 | 5/2009 | Pettis et al. | |
| 2009/0163855 A1 | 6/2009 | Shin et al. | |
| 2009/0163874 A1 | 6/2009 | Krag et al. | |
| 2009/0171324 A1 | 7/2009 | Chong et al. | |
| 2009/0182277 A1 | 7/2009 | Carter | |
| 2009/0192471 A1 | 7/2009 | Carter et al. | |
| 2009/0198215 A1 | 8/2009 | Chong et al. | |
| 2009/0326454 A1 | 12/2009 | Cross et al. | |
| 2009/0326455 A1 | 12/2009 | Carter | |
| 2009/0326472 A1 * | 12/2009 | Carter et al. | 604/180 |
| 2010/0007248 A1 | 1/2010 | Chiang et al. | |
| 2010/0022992 A1 | 1/2010 | Genosar et al. | |
| 2010/0063438 A1 | 3/2010 | Bengtsson | |
| 2010/0087778 A1 * | 4/2010 | Genosar et al. | 604/65 |
| 2010/0129699 A1 | 5/2010 | Mikhaylik et al. | |
| 2010/0304215 A1 | 12/2010 | Suh et al. | |
| 2011/0042204 A1 | 2/2011 | Chiang et al. | |
| 2011/0098643 A1 | 4/2011 | Chiang et al. | |
| 2011/0098676 A1 | 4/2011 | Chiang et al. | |

FOREIGN PATENT DOCUMENTS

| | | |
|---|---|---|
| DE | 10026264 | 11/2001 |
| EP | 1621875 | 2/2006 |
| EP | 2015806 | 9/2009 |
| JP | 4-127885 | 4/1992 |
| JP | 1-144342 | 5/2001 |
| WO | WO 95/15589 | 6/1995 |
| WO | WO 96/34417 | 10/1996 |
| WO | WO 2004/067066 | 8/2004 |
| WO | WO 2005/124918 | 12/2005 |
| WO | WO 2006/123329 | 11/2006 |
| WO | WO 2007/010522 | 1/2007 |
| WO | WO 2007/111880 | 10/2007 |
| WO | WO 2007/129317 | 11/2007 |
| WO | WO 2008/036122 | 3/2008 |
| WO | WO 2008/094196 | 8/2008 |
| WO | WO 2008/129549 | 10/2008 |
| WO | WO 2009/123672 | 10/2009 |

OTHER PUBLICATIONS

Codman 3000, Johnson & Johnson Company.
Osborne, R., "Valeritas' Insulin Patch Takes Aim At Type II Drug Resisters," BioWorld Financial Watch, Sep. 4, 2006, vol. 14, No. 36, Atlanta, Georgia.
Barvosa-Carter, W. et al., "Solid-state actuation based on reversible Li electroplating," Smart Structures and Materials 2005: Active Materials: Behavior and Mechanics, Proceedings of SPIE, 5761, pp. 90-97.
Baughman, R.H., "Conducting Polymer Artificial Muscles," Synthetic Metals, 1996, pp. 339-353, vol. 78.
Bruesewitz, M., "Elektrochmische Aktoren," F&M Feinwerktechnik Mikrotechnik, Hanser, Munchen, DE, Jul. 1, 1998, pp. 527-530, vol. 106(7/08).
Che, G. et al., "An Electrochemically Driven Actuator Based on a Nanostructured Carbon Material," Anal. Chem., 1999, pp. 3187-3191, vol. 71.
Chin, T.E. et al., "Lithium Rechargeable Batteries as Electromechanical Actuators," Electrochemical and Solid State Letters, 2006, pp. A134-A138, vol. 9(3).
Gu, G. et al., "$V_2O_5$ Nanofibre Sheet Actuators," Nature Materials, 2003, pp. 316-319, vol. 2.
Koyama, Y. et al., "Harnessing the Actuation Potential of Solid-State Intercalation Compounds," Adv. Funct. Mater., 2006, pp. 492-498, vol. 16.
Lin, K. et al., "Towards Electrochemical Artificial Muscles: A Supramolecular Machine Based on a One-Dimensional Copper-Containing Organophosphonate System," Angew. Chem. Int. Ed., 2004, pp. 4186-4189, vol. 43.
Massey, C. et al., "Graphite Intercalation Compounds as Actuation Materials," 2004 Proceedings of IMECE04: 2004 ASME International Mechanicla Engineering Congress and Exposition, pp. 117-122.
Massey, C. et al., "Reversible Work by Electromchemical Intercalation of Graphitic Materials," Smart Structures and Materials 2005: Electroactive Polymer Actuators and Devices (EAPAD), Proceedings of SPIE, pp. 322-330, vol. 5759.
Niezrecki, C. et al., "Piezoelectric Actuation: State of the Art," The Shock and Vibration Digest, Jul. 2001, pp. 269-280, vol. 33(4).
Paquette, J.W. et al., "Ionomeric Electroactive Polymer Artificial Muscle for Naval Applications," IEEE Journal of Oceanic Engineering, 2004, pp. 729-737, vol. 29(3).
Prechtl, E. et al., "Design of a High Efficiency, Large Stroke, Electrochemical Actuator," Smart Mater. Struct., 1999, pp. 13-30, vol. 8.
Shahinpoor, M. et al., "Ionic Polymer-Metal Composites (IPMC) As Biomimetic Sensors and Actuators," Proceedings of SPIE's 5th Annual International Symposium on Smart Structures and Materials, Mar. 1-5, 1998, San Diego, CA, Paper No. 3324-27.
Spinks, G.M. et al., "Pheumantic Carbon Nanotube Actuators," Adv. Mater., 2002, pp. 1728-1732, vol. 14(23).
Takada, K. et al., "Electrochemical Actuator with Silver Vanadium Bronzes," Solid State Ionics, 1992, pp. 339-342, vol. 53-56.
Thomson, E.A., "Moving Toward Morphing Vehicles," MIT TechTalk, Mar. 22, 2006, pp. 1-8, vol. 50(21).
Yamada, A. et al., "Optimized $LiFePO_4$ for Lithium Battery Cathodes," Journal of the Electrochemical Society, 2001, pp. A224-A229, vol. 148(3).
Office Action mailed Aug. 20, 2009, for U.S. Appl. No. 12/181,085 (10 pages).
Office Action mailed Mar. 24, 2010, for U.S. Appl. No. 12/181,085 (9 pages).
International Search Report and Written Opinion for International Application No. PCT/US2008/071368, mailed Mar. 25, 2009.
Supplementary European Search Report for European Patent Application No. EP 05758772, mailed Mar. 5, 2010 (4 pages).
International Preliminary Report on Patentability for International Application No. PCT/US2005/020554, mailed Mar. 4, 2008 (5 pages).
International Search Report and Written Opinion for International Application No. PCT/US2005/020554 (corrected copy), mailed Feb. 7, 2008 (11 pages).
Office Action mailed Jun. 17, 2010, for U.S. Appl. No. 11/796,138 (4 pages).
International Preliminary Report on Patentability for International Application No. PCT/US2007/010036, mailed Oct. 28, 2008 (8 pages).
International Search Report and Written Opinion for International Application No. PCT/US2007/010036, mailed May 21, 2008 (17 pages).
International Preliminary Report on Patentability for International Application No. PCT/US2007/016849, mailed Feb. 5, 2009 (6 pages).
International Search Report and Written Opinion for International Application No. PCT/US2007/016849, mailed Sep. 24, 2008 (12 pages).
Office Action mailed Jun. 16, 2010, for U.S. Appl. No. 12/035,406 (4 pages).
International Preliminary Report on Patentability for International Application No. PCT/US2009/001075, dated Aug. 24, 2010, mailed Sep. 2, 2010.
International Search Report and Written Opinion for International Application No. PCT/US2009/001075, mailed May 25, 2010, 13 pages.
Office Action mailed Mar. 11, 2010, for U.S. Appl. No. 12/208,180 (5 pages).

\* cited by examiner

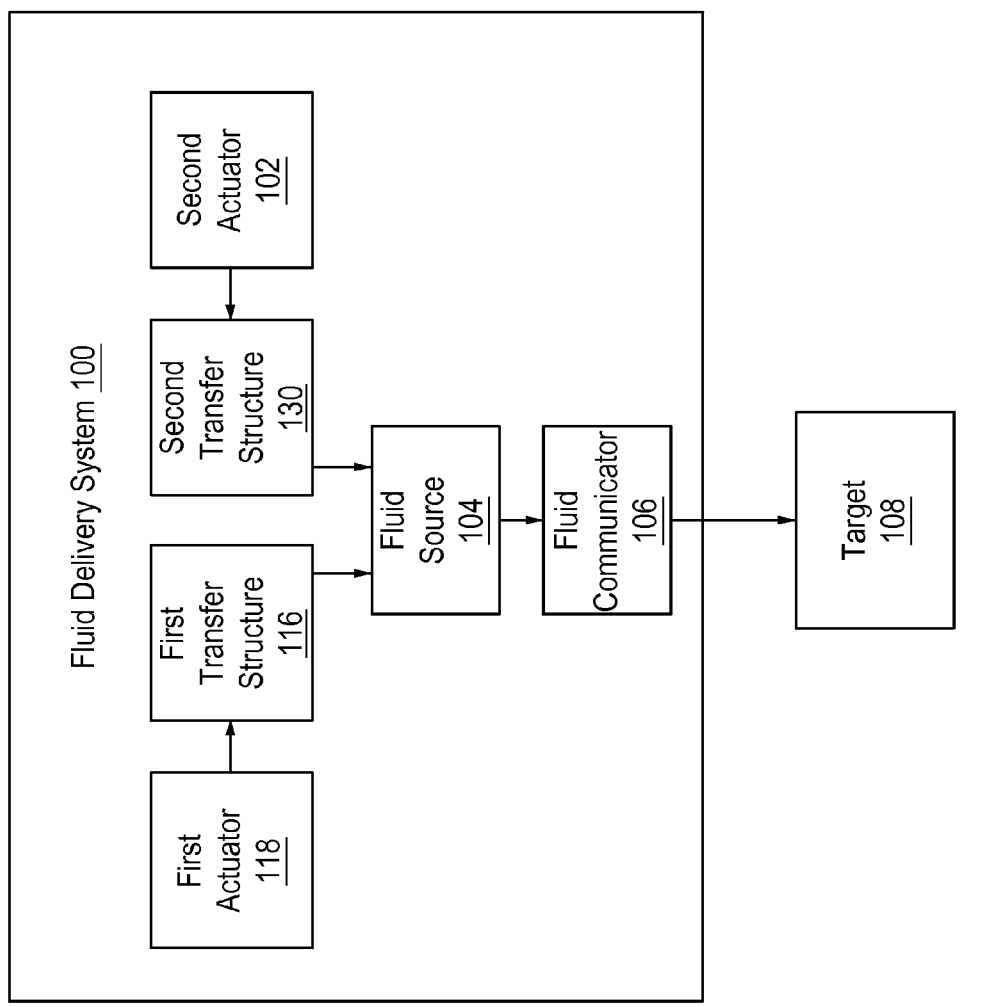

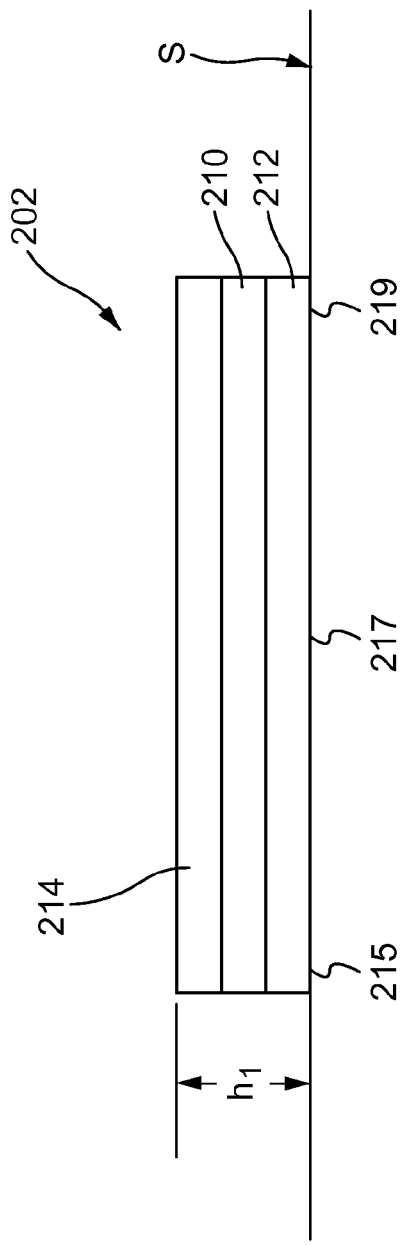
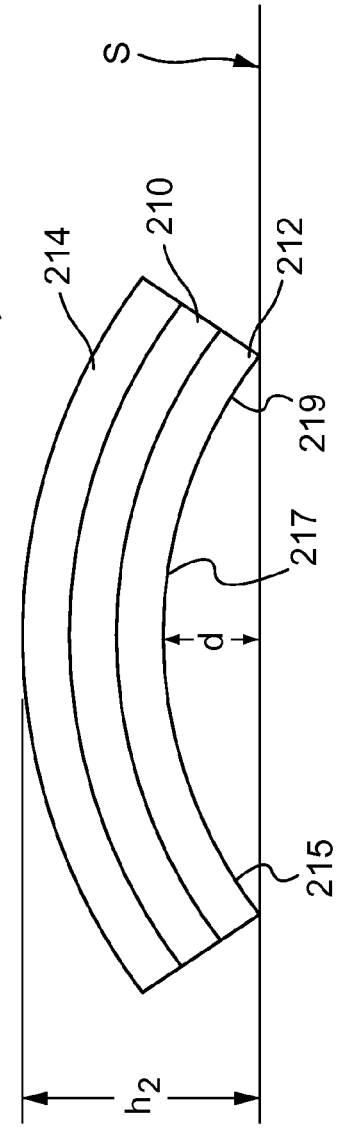

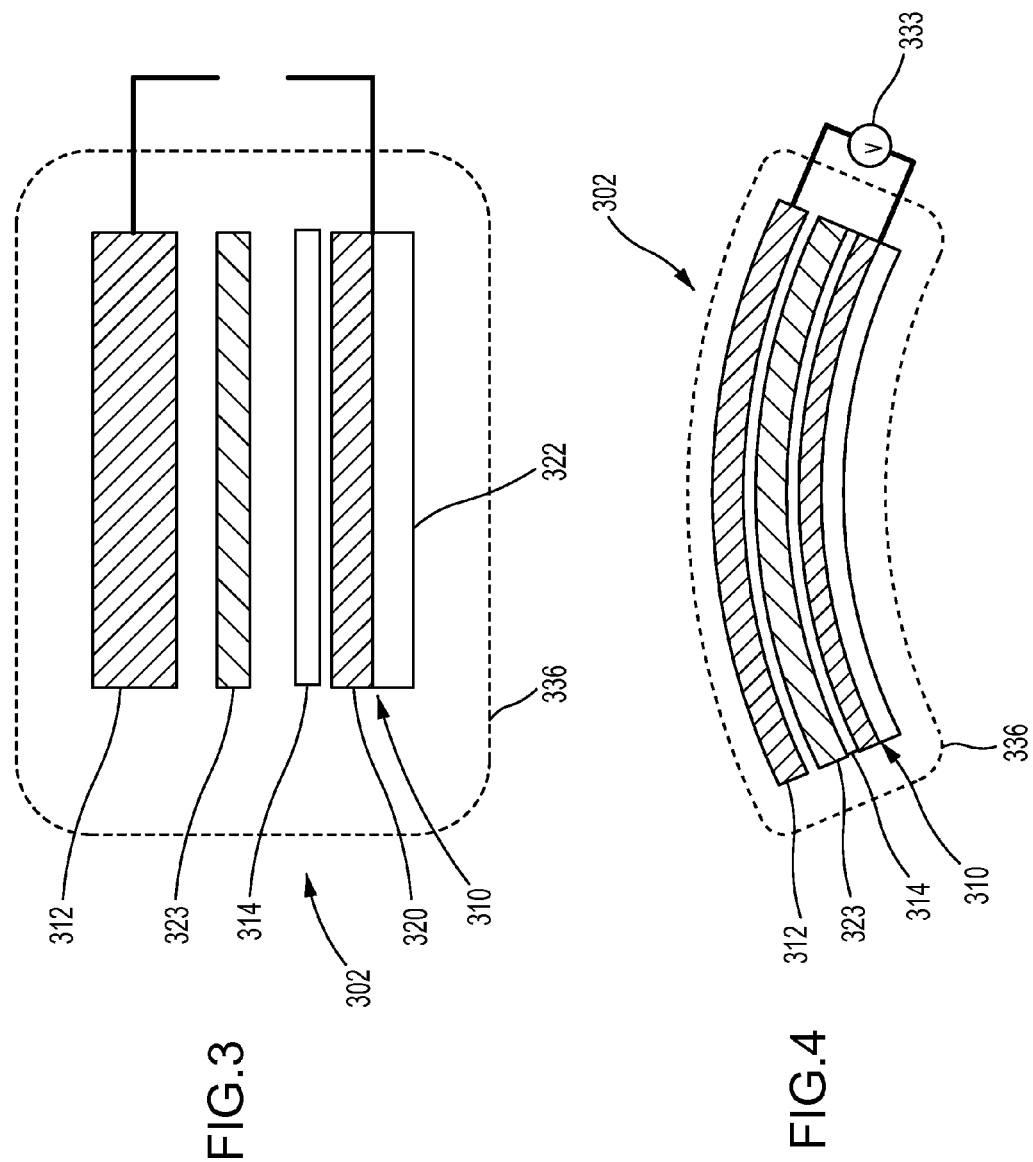

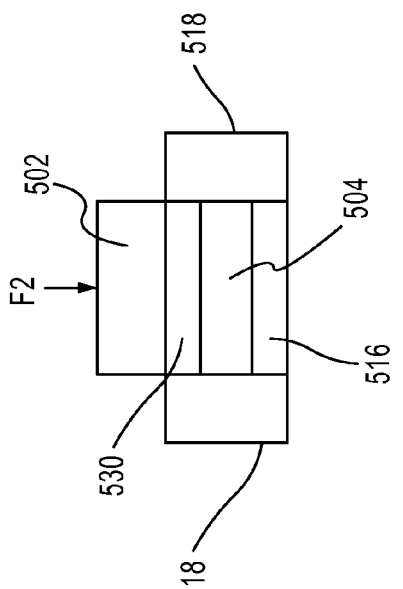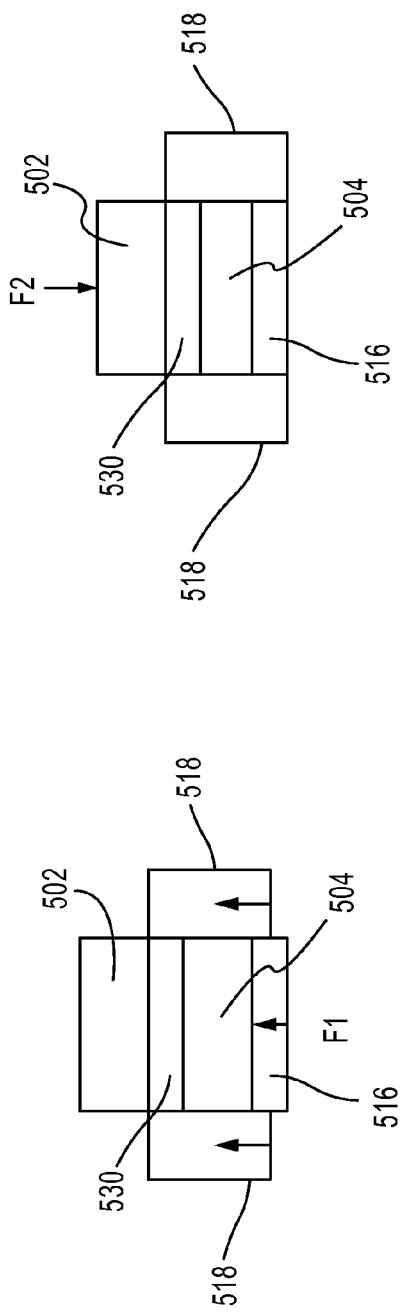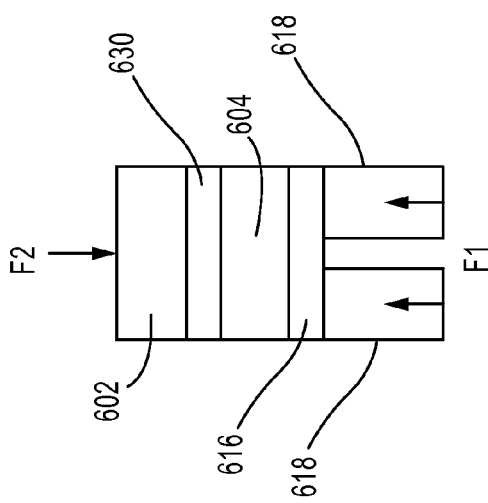

SYSTEMS AND METHODS FOR DELIVERING A THERAPEUTIC AGENT

CROSS-REFERENCE TO RELATED APPLICATION

This application claims priority to and the benefit of U.S. Provisional Application Ser. No. 61/331,763, filed May 5, 2010, entitled "Systems and Methods for Delivering a Therapeutic Agent," the disclosure of which is hereby incorporated by reference herein in its entirety.

BACKGROUND

The invention relates generally to medical devices and procedures, including, for example, medical devices and methods for delivering a therapeutic agent to a patient.

Drug delivery involves delivering a drug or other therapeutic compound into the body. Typically, the drug is delivered via a technology that is carefully selected based on a number of factors. These factors can include, but are not limited to, the characteristics of the drug, such as drug dose, pharmacokinetics, complexity, cost, and absorption, the characteristics of the desired drug delivery profile (such as uniform, non-uniform, or patient-controlled), the characteristics of the administration mode (such as the ease, cost, complexity, and effectiveness of the administration mode for the patient, physician, nurse, or other caregiver), or other factors or combinations of these factors.

Conventional drug delivery technologies present various challenges. Oral administration of a dosage form is a relatively simple delivery mode, but some drugs may not achieve the desired bioavailability and/or may cause undesirable side effects if administered orally. Further, the delay from time of administration to time of efficacy associated with oral delivery may be undesirable depending on the therapeutic need. While parenteral administration by injection may avoid some of the problems associated with oral administration, such as providing relatively quick delivery of the drug to the desired location, conventional injections may be inconvenient, difficult to self-administer, and painful or unpleasant for the patient. Furthermore, injection may not be suitable for achieving certain delivery/release profiles, particularly over a sustained period of time.

In addition, the immediate delivery of a full dose of a drug may cause undesirable side effects related to the very high peak plasma concentration resulting from the bolus injection. If this peak concentration is blunted by delivering the dose over an extended period of time, the side effects may be ameliorated and make the treatment much more tolerable, and in some cases, it may allow higher doses to be delivered, thus increasing the efficacy of the drug. If a high bolus dose is required in order to attain extended efficacy of the drug as it is eliminated from the body (i.e., to maintain a minimum trough level of drug), then by extending the delivery time, the trough level may be maintained with a lower total dose of drug. Thus, the same efficacy may be achieved at a lower total dose of the drug and result in a larger margin of safety.

Passive transdermal technology, such as a conventional transdermal patch, may be relatively convenient for the user and may permit relatively uniform drug release over time. However, some drugs, such as highly charged or polar drugs, peptides, proteins and other large molecule active agents, may not penetrate the stratum corneum for effective delivery. Furthermore, a relatively long start-up time may be required before the drug takes effect. Thereafter, the drug release may be relatively continuous, which may be undesirable in some cases. Also, a substantial portion of the drug payload may be undeliverable and may remain in the patch once the patch is removed.

Active transdermal systems, including iontophoresis, sonophoresis, and poration technology, may be expensive and may yield unpredictable results. Only some drug formulations, such as aqueous stable compounds, may be suited for active transdermal delivery. Further, modulating or controlling the delivery of drugs using such systems may not be possible without using complex systems.

Some infusion pump systems may be large and may require tubing between the pump and the infusion set, which can impact the quality of life of the patient. Further, infusion pumps may be expensive and may not be disposable. From the above, it would be desirable to provide new and improved drug delivery systems and methods that overcome some or all of these and other drawbacks.

SUMMARY OF THE INVENTION

Devices, methods, and kits for delivering a therapeutic agent to a patient are disclosed herein. In one embodiment, an apparatus comprises a reservoir for containing a fluid, a first actuator, a transfer structure, and a second actuator. The first actuator has a first configuration and a second configuration and is configured to exert a first force on the reservoir when moved from its first configuration to its second configuration such that a first volume of fluid within the reservoir is communicated out of the fluid reservoir. The transfer structure is disposed between the first actuator and the reservoir and has a surface configured to engage the reservoir such that the first force exerted by the first actuator is distributed across a surface of the reservoir engaged by the transfer structure. The second actuator has a first configuration and a second configuration and is configured to exert a second force on the reservoir when the second actuator is moved from its first configuration to its second configuration such that a second volume of fluid within the reservoir is communication out of the fluid reservoir.

BRIEF DESCRIPTION OF THE DRAWINGS

FIG. 1 is a schematic illustration of a delivery system according to an embodiment.

FIG. 2(a) is side view of a schematic illustration of an electrochemical actuator shown in a charged state; and FIG. 2(b) is a schematic illustration of a side view of the electrochemical actuator of FIG. 2(a) shown in a discharged state.

FIG. 3 is a schematic illustration of a portion of a delivery system according to an embodiment illustrating an electrochemical actuator in a charged state.

FIG. 4 is a schematic illustration of the portion of the delivery system of FIG. 3 illustrating the electrochemical actuator as it discharges.

FIG. 22A is a schematic illustration of the delivery device of FIG. 5 showing the forces exerted by a first actuator; and FIG. 22B is a schematic illustration of the delivery device of FIG. 5 showing the forces exerted by a second actuator.

FIG. 23 is a schematic illustration of an embodiment of a delivery device showing the forces exerted by a first actuator and the forces exerted by a second actuator.

DETAILED DESCRIPTION

Figure 5:
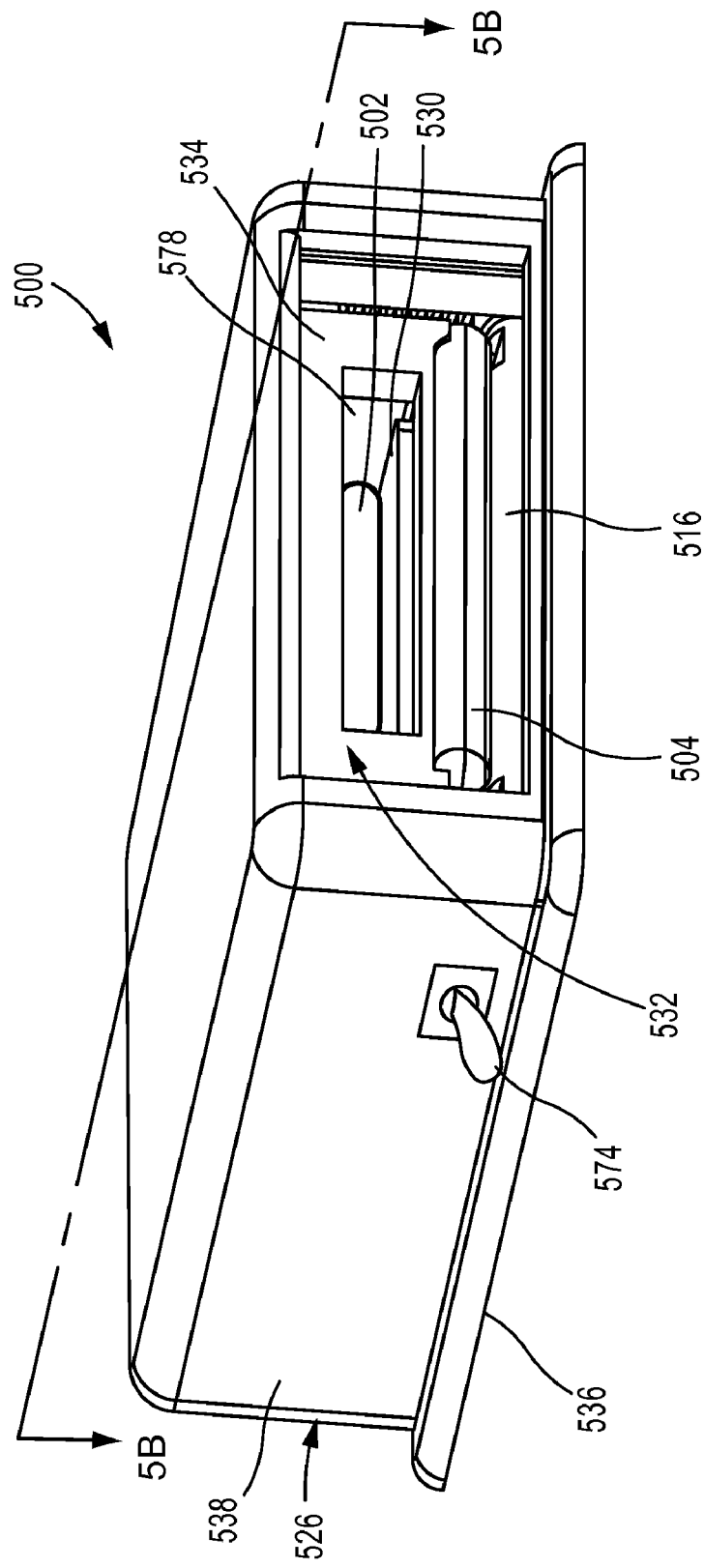
FIG. 5 is a perspective view of a delivery device according to an embodiment.
Figure 7:
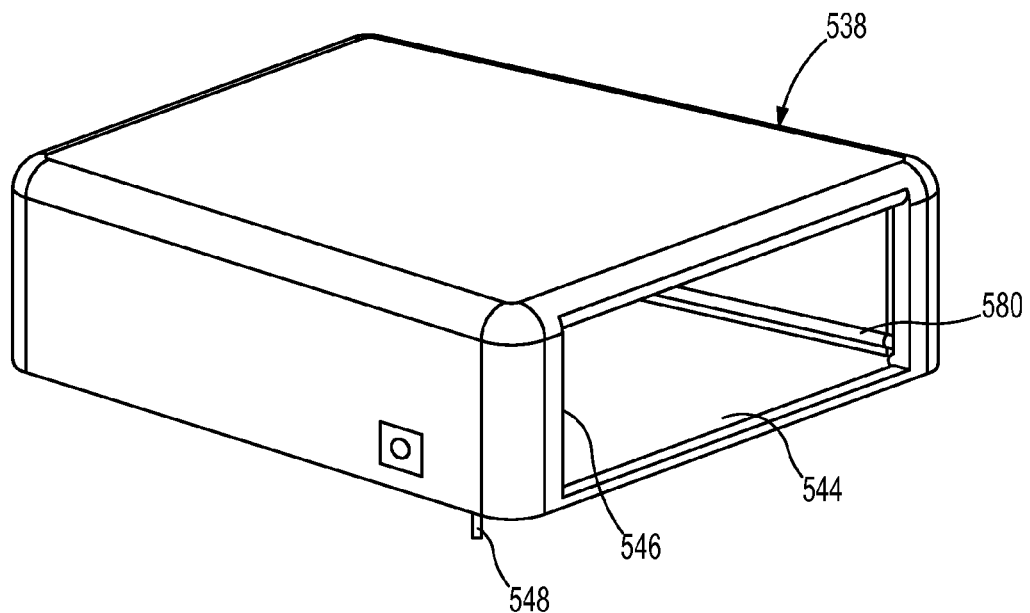
FIG. 7 is a front perspective view of a cover member of the delivery device of FIG. 5.

Devices, systems, methods and kits are described herein that are configured for use in the delivery of therapeutic agents to a patient's body. Such therapeutic agents can be, for example, one or more drugs and can be in fluid form of various viscosities. In some embodiments, the devices and methods can include a pump device that includes an actuator, such as, for example, an electrochemical actuator, which can have characteristics of both a battery and a pump. Specifically, an electrochemical actuator can include an electrochemical cell that produces a pumping force as the cell discharges. Thus, the pump device can have relatively fewer parts than a conventional drug pump, such that the pump device is relatively more compact, disposable, and reliable than conventional drug pumps. Such drug delivery devices are desirable, for example, for use in delivery devices that are designed to be attached to a patient's body (e.g., a wearable device). These attributes of the pump device may reduce the cost and the discomfort associated with infusion drug therapy.

In some embodiments, such a pump device can be operated with, for example, a controller and/or other circuitry, operative to regulate drug or fluid flow from the pump device. Such a controller may permit implementing one or more release profiles using the pump device, including release profiles that require uniform flow, non-uniform flow, continuous flow, discontinuous flow, programmed flow, scheduled flow, user-initiated flow, or feedback responsive flow, among others. Thus, the pump device may effectively deliver a wider variety of drug therapies than other pump devices.

In some embodiments, a drug delivery system can include one or more actuators. For example the delivery system can include one or more electrochemical actuators or one or more electrochemical actuators and one or more mechanical actuators employing a mechanical energy storage mechanism, such as springs or elastomeric members. In some embodiments, a first actuator can be actuated to provide a first phase of pumping at a first rate, and then a second actuator can be actuated to provide a second phase of pumping at a second rate, which may be the same as, or different than, the first rate. In alternative embodiments, the first and second actuators can be actuated at the same time or at different times. The first actuator can be, for example, a mechanical actuator (e.g., spring-based) and the second actuator can be, for example, an electrochemical actuator, or vice versa. In some embodiments, a mechanical actuator can provide a faster rate of delivery than the delivery provided by an electrochemical actuator. Thus, a combination of fast and slow delivery rates can be achieved. In some embodiments, an electrochemical actuator may provide a faster rate of delivery than a mechanical, spring-based actuator. Mechanical actuators can also be configured to apply a greater force on the fluid reservoir containing the drug to be delivered. In some embodiments, one or more electrochemical actuators can be used in sequence or simultaneously.

The multi-phase drug delivery systems described herein can be used to deliver medications and provide treatments at different rates within the same device such as a bolus followed by a uniform slow delivery over a specified time period. The delivery systems can be used to deliver larger doses than other known delivery systems, providing enhanced treatment options.

FIG. 1 is a schematic block diagram illustrating an embodiment of a fluid delivery system 100 (also referred to herein as "delivery device" or "drug delivery device"). The fluid delivery system 100 can include a first actuator 118, a second actuator 102, a first transfer structure 116, a second transfer structure 130, a fluid source 104 and a fluid communicator 106. The first actuator 118 can be for example, a mechanical actuator, such as one using a spring as a source of stored mechanical energy, and the second actuator 102 can be, for example, an electrochemical actuator, as described in more detail below. The fluid source 104 can contain a fluid (i.e., a therapeutic agent) to be delivered into a target 108 via the fluid communicator 106. The target 108 can be, for example, a human or other mammalian body in need of a drug therapy or prophylaxis.

The second actuator 102 (also referred to herein as "electrochemical actuator 102") can actuate or otherwise create a pumping force to deliver the fluid from the fluid source 104 into the fluid communicator 106 as described in more detail below. In some embodiments, the electrochemical actuator 102 can be a device that experiences a change in volume or position in response to an electrochemical reaction that occurs therein. For example, the electrochemical actuator 102 can include a charged electrochemical cell, and at least a portion of the electrochemical cell can actuate as the electrochemical cell discharges. Thus, the electrochemical actuator 102 can be considered a self-powered actuator or a combination battery and actuator. In some embodiments, more than one electrochemical actuator can be included.

For illustration and discussion purposes, the first actuator 118 is also referred to herein as "spring-based actuator 118." As discussed above, the spring-based actuator 118 can be used in conjunction with the electrochemical actuator 102 to provide variable or multi-phase delivery rates. Thus, distinct delivery rates can be achieved that may not otherwise be available with a single actuator without the use of complex valve/control systems to meter flow-rate outputs. Various delivery rates and delivery sequences can be customized to meet the particular drug delivery need. For example, in some embodiments, a drug delivery system can be configured to deliver a drug at a first delivery rate during actuation of the first actuator 118 that is different than (e.g. greater than) a second delivery rate during actuation of the electrochemical actuator 102. In some embodiments, a drug delivery system can be configured to deliver a drug at a first rate that is slower than a second rate or at a first rate that is faster than a second rate. In some embodiments, a mechanical actuator can be configured to deliver a loading dose at a relatively fast rate during a start-up phase of an electrochemical actuator until the electrochemical actuator arrives at a steady-state delivery rate. The electrochemical actuator alone or in combination with the mechanical actuator can then complete delivery of the remaining dose at a relatively lower basal delivery rate. Specific embodiments of a spring-based actuator and electrochemical actuator are described in more detail below.

The fluid source 104 can be a reservoir, pouch, chamber, barrel, bladder, or other known device that can contain a drug in fluid form therein. The fluid communicator 106 can be in, or can be moved into, fluid communication with the fluid source 104. The fluid communicator 106 can be, for example, a needle, catheter, cannula, infusion set, or other known drug delivery conduit that can be inserted into or otherwise associated with the target body for drug delivery.

In some embodiments, the fluid source 104 can be any component capable of retaining a fluid or drug in fluid form. In some embodiments, the fluid source 104 may be disposable (e.g., not intended to be refillable or reusable). In other embodiments, the fluid source 104 can be refilled, which may permit reusing at least a portion of the device and/or varying the drug or fluid delivered by the device. In some embodiments, the fluid source 104 can be sized to correlate with the electrochemical potential of the electrochemical actuator 102 and the stroke of the spring-based actuator 118. For example, the size and/or volume of the fluid source 104 can be selected so that the fluid source 104 becomes about substantially empty at about the same time that the aggregate actuation of the spring-based actuator 118 and electrochemical actuator 102 is complete. By optimizing the size of the fluid source 104 and the amount of drug contained therein to correspond to the driving potential of the electrochemical actuator 102 and the stroke of the spring-based actuator 118, the size and/or cost of the device may be reduced. In other embodiments, the electrochemical actuator 102 and/or the spring-based actuator 118 may be oversized with reference to the fluid source 104. In some embodiments, the delivery system 100 can include more than one fluid source 104. Such a configuration may permit using a single device to deliver two or more drugs or fluids. The two or more drugs or fluids can be delivered discretely, simultaneously, alternating, according to a program or schedule, or in any other suitable manner. In such embodiments, the fluid sources 104 may be associated with the same or different electrochemical actuators 102, the same or different spring-based actuators 118, the same or different fluid communicators 106, the same or different operational electronics, or the same or different portions of other components of the delivery system.

The first transfer structure 116 can be disposed such that a surface of the transfer structure 116 can contact the fluid source 104 when the first actuator (e.g., spring-based actuator) 118 is actuated. For example, the spring-based actuator 118 can include one or more springs that are coupled to the transfer structure 116 and when the spring-based actuator 118 is actuated, the springs can apply a pulling force (if extension springs are used) or a pushing force (if compression springs are used) on the first transfer structure 116, which in turn will act upon the fluid source 104, as described in more detail below. The first transfer structure 116 can include one or more components. For example, the transfer structure 116 can be a single component having a surface configured to contact the fluid source 104. In some embodiments, the transfer structure 116 can include one or more members having a surface configured to contact the fluid source 104 upon activation of the spring-based actuator 118. In some embodiments, the transfer structure 116 is a substantially planar or flat plate.

The second transfer structure 130 can be disposed between the electrochemical actuator 102 and the fluid source 104. In some embodiments, the second transfer structure 130 includes a surface configured to contact a side of the fluid source 104 opposite to the side contacted by the first transfer structure 116 upon actuation of the electrochemical actuator 102 such that a force exerted by the electrochemical actuator 102 is transferred from the transfer structure 130 to the fluid source 104. The transfer structure 130 can include one or more components. For example, the transfer structure 130 can be a single component having a surface configured to contact the fluid source 104. In some embodiments, the transfer structure 130 can include one or more members having a surface configured to contact the fluid source 104 upon activation of the electrochemical actuator 102. In some embodiments, the transfer structure 130 is a substantially planar or flat plate.

In some embodiments, the fluid delivery system 100 can be used to deliver a drug formulation which comprises a drug, including an active pharmaceutical ingredient. In other embodiments, the fluid delivery system 100 may deliver a fluid that does not contain a drug. For example, the fluid may be a saline solution or a diagnostic agent, such as a contrast agent. Drug delivery can be subcutaneous, intravenous, intraarterial, intramuscular, intracardiac, intraosseous, intradermal, intrathecal, intraperitoneal, intratumoral, intratympnic, intraaural, topical, epidural, and/or peri-neural depending on, for example, the location of the fluid communicator 106 and/or the entry location of the drug.

The drug (also referred to herein as "a therapeutic agent" or "a prophylactic agent") can be in a pure form or formulated in a solution, a suspension, or an emulsion, among others, using one or more pharmaceutically acceptable excipients known in the art. For example, a pharmaceutically acceptable vehicle for the drug can be provided, which can be any aqueous or non-aqueous vehicle known in the art. Examples of aqueous vehicles include physiological saline solutions, solutions of sugars such as dextrose or mannitol, and pharmaceutically acceptable buffered solutions, and examples of non-aqueous vehicles include fixed vegetable oils, glycerin, polyethylene glycols, alcohols, and ethyl oleate. The vehicle may further include antibacterial preservatives, antioxidants, tonicity agents, buffers, stabilizers, or other components.

Although the fluid delivery system 100 and other systems and methods described herein are generally described as communicating drugs into a human body, such systems and methods may be employed to deliver any fluid of any suitable biocompatibility or viscosity into any object, living or inanimate. For example, the systems and methods may be employed to deliver other biocompatible fluids into living beings, including human beings and other animals. Further, the systems and methods may deliver drugs or other fluids into living organisms other than human beings, such as animals and plant life. Also, the systems and methods may deliver any fluids into any target, living or inanimate.

The systems and methods described herein are generally systems and methods of delivering fluids using a delivery device 100 that includes an electrochemical actuator 102, such as a self-powered actuator and/or combined battery and actuator. Example embodiments of such electrochemical actuators are generally described in U.S. Pat. No. 7,541,715, entitled "Electrochemical Methods, Devices, and Structures" by Chiang et al., U.S. Patent Pub. No. 2008/0257718, entitled "Electrochemical Actuator" by Chiang et al., and U.S. Patent Pub. No. 2009/0014320, entitled "Electrochemical Actuator" by Chiang et al., and U.S. Pat. No. 7,828,771, entitled "Systems and Methods for Delivering Drugs" by Chiang et al. (the '771 patent"), the disclosure of each of which is incorporated herein by reference. Such electrochemical actuators can include at least one component that responds to the application of a voltage or current by experiencing a change in volume or position. The change in volume or position can produce mechanical work that can then act on a fluid source (e.g., fluid source 104) or may be transferred to a fluid source, such that a fluid can be delivered out of the fluid source.

In some embodiments, the electrochemical actuator 102 can include a positive electrode and a negative electrode, at least one of which is an actuating electrode. These and other components of the electrochemical actuator can form an electrochemical cell, which can in some embodiments initially be charged. For example, the electrochemical cell may begin discharging when a circuit between the electrodes is closed, causing the actuating electrode to actuate. The actuating electrode can thereby perform work upon another structure, such as the fluid source, or a transfer structure associated with the fluid source, as described in more detail below. The work can then cause fluid to be pumped or otherwise dispensed from the fluid source into the target 108.

More specifically, the actuating electrode of the electrochemical actuator 102 can experience a change in volume or position when the closed circuit is formed, and this change in volume or position can perform work upon the fluid source or transferring structure. For example, the actuating electrode may expand, bend, buckle, fold, cup, elongate, contract, or otherwise experience a change in volume, size, shape, orientation, arrangement, or location, such that at least a portion of the actuating electrode experiences a change in volume or position. In some embodiments, the change in volume or position may be experienced by a portion of the actuating electrode, while the actuating electrode as a whole may experience a contrary change or no change whatsoever. It is noted that the delivery device 100 can include more than one electrochemical actuator 102. For example, in some embodiments, the delivery device 100 can include one or more electrochemical actuators 102 arranged in series, parallel, or some combination thereof. In some embodiments, a number of such electrochemical actuators 102 may be stacked together. As another example, concurrent or sequenced delivery of multiple agents can be achieved by including one or more electrochemical actuators 102 acting on two or more fluid sources.

The spring-based actuator 118 can include one or more springs (not shown in FIG. 1) that are operatively coupled to the first transfer structure 116. A variety of different types of springs can be used, for example, compression, extension, spring washers, Belleville, tapered, or other types of springs to achieve a desired delivery rate. In addition, a variety of elastomeric structures can be used in a variety of configurations to provide either a "pulling" or "pushing" force on the fluid source 104. The spring-based actuator 118 can be configured to apply a force on the first transfer structure 116 such that when the actuator 118 is activated the force is transferred from the first transfer structure 116 to the fluid source 104. For example, the springs can initially be moved to a pre-loaded state and then allowed to move back towards an un-biased state. During this transition, the springs can apply a force (e.g., a pulling force or a pushing force) on the first transfer structure 116. The details and function of the spring-based actuator 118 are described in more detail below with reference to specific embodiments.

The delivery system 100 can also include a housing (not shown in FIG. 1) that can be removably or releasably attached to the skin of the patient. The various components of the delivery system 100 can be fixedly or releasably coupled to the housing. To adhere the delivery device 100 to the skin of a patient, a releasable adhesive can at least partially coat an underside of the housing. The adhesive can be non-toxic, biocompatible, and releasable from human skin. To protect the adhesive until the device is ready for use, a removable protective covering can cover the adhesive, in which case the covering can be removed before the device is applied to the skin. Alternatively, the adhesive can be heat or pressure sensitive, in which case the adhesive can be activated once the device is applied to the skin. Example adhesives include, but are not limited to, acrylate based medical adhesives of the type commonly used to affix medical devices such as bandages to skin However, the adhesive is not necessary, and may be omitted, in which case the housing can be associated with the skin, or generally with the body, in any other manner. For example, a strap or band can be used.

The housing can be formed from a material that is relatively lightweight and flexible, yet sturdy. The housing also can be formed from a combination of materials such as to provide specific portions that are rigid and specific portions that are flexible. Example materials include plastic and rubber materials, such as polystyrene, polybutene, carbonate, urethane rubbers, butene rubbers, silicone, and other comparable materials and mixtures thereof, or a combination of these materials or any other suitable material can be used.

In some embodiments, the housing can include a single component or multiple components. In some embodiments, the housing can include two portions: a base portion and a movable portion. The base portion can be suited for attaching to the skin. For example, the base portion can be relatively flexible. An adhesive can be deposited on an underside of the base portion, which can be relatively flat or shaped to conform to the shape of a particular body part or area. The movable portion can be sized and shaped for association with the base portion. In some embodiments, the two portions can be designed to lock together, such as via a locking mechanism. In some cases, the two portions can releasably lock together, such as via a releasable locking mechanism, so that the movable portion can be removably associated with the base portion. To assemble such a housing, the movable portion can be movable with reference to the base portion between an unassembled position and an assembled position. In the assembled position, the two portions can form a device having an outer shape suited for concealing the device under clothing. Various example embodiments of a housing are described in the '771 patent.

The delivery system 100 can also include a cartridge (not shown in FIG. 1) that can be coupled to the housing. The cartridge can define an interior region to contain various components of the delivery device 100. For example, in some embodiments, the electrochemical actuator 102 and/or transfer plate 130 are disposed within the cartridge. In some embodiments, the fluid source 104 can also be contained within the cartridge. For example, in some embodiments, a housing can define an interior region and contain the transfer structure 116 and a spring actuator 130. A cartridge containing an electrochemical actuator 102, a transfer plate 130 and the fluid source 104 can be sized and configured to be received within the interior region of the housing such that the fluid source is adjacent the transfer structure 116. Specific embodiments of such a delivery system 100 are described in more detail below. An insertion mechanism for inserting the fluid communicator 106 into a patient's body can also be contained within an interior region of the housing or the cartridge.

The size, shape, and weight of the delivery device 100 can be selected so that the delivery device 100 can be comfortably worn on the skin after the device is applied via the adhesive. For example, the delivery device 100 can have a size, for example, in the range of about 1.0"×1.0"×0.1" to about 5.0"×5.0"×1.0", and in some embodiments in a range of about 2.0"×2.0"×0.25" to about 4.0"×4.0"×0.67". The weight of the delivery device 100 can be, for example, in the range of about 5 g to about 200 g, and in some embodiments in a range of about 15 g to about 100 g. The delivery device 100 can be configured to dispense a volume in the range of about 0.1 ml to about 1,000 ml, and in some cases in the range of about 0.3 ml to about 100 ml, such as between about 0.5 ml and about 5 ml. The shape of the delivery device 100 can be selected so that the delivery device 100 can be relatively imperceptible under clothing. For example, the housing can be relatively smooth and free from sharp edges (see, for example, FIG. 11). However, other sizes, shapes, and/or weights are possible.

As mentioned above, a first actuator 118 (e.g., a spring-based actuator) and a second actuator 102 (e.g., an electrochemical actuator) can be used to cause the fluid delivery device 100 to deliver a drug-containing or non-drug containing fluid into a human patient or other target 108. Such a fluid delivery system 100 can be embodied in a relatively small, self-contained, and disposable device, such as a patch device that can be removably attached to the skin of a patient as described above. The delivery device 100 can be relatively small and self-contained, in part, because the electrochemical actuator 102 serves as both the battery and a pump and the spring-based actuator 118 can be sized to occupy a relatively small area of the device. The small and self-contained nature of the delivery device 100 advantageously may permit concealing the device beneath clothing and may allow the patient to continue normal activity as the drug is delivered. Unlike conventional drug pumps, external tubing to communicate fluid from the fluid reservoir into the body can be eliminated. Such tubing can instead be contained within the delivery device, and a needle or other fluid communicator can extend from the device into the body. The small and inexpensive nature of the components of the device may, in some embodiments, permit disposing of the entire device after a single use. The delivery device 100 can permit drug delivery, such as subcutaneous or intravenous drug delivery, over a time period that can vary from several minutes to several days. Subsequently, the delivery device 100 can be removed from the body and discarded.

In use, the delivery device 100 can be placed in contact with the target 108 (e.g. placed on the surface of a patient's body), such that the fluid communicator 106 (e.g., a needle, cannula, etc.) is disposed adjacent to a desired injection site. The fluid communicator 106 can be activated such that it is inserted into the patient's body. The spring-based actuator 118 can be actuated such that it applies a force on the transfer structure 116 moving the transfer structure in a direction toward the fluid source 104. The force is then transferred from the transfer structure 116 to the fluid source 104, causing fluid in the fluid source 104 to be delivered through the fluid communicator 106 and into the target 108 at a first rate during a first time period. The actuation of the spring-based actuator 118 can continue, for example, until the transfer structure 116 reaches a mechanical stop within the delivery device 100. The electrochemical actuator 102 can then be actuated to apply a force on the fluid source 104, causing the fluid to be delivered through the fluid communicator 106 into the target 108 at a second rate during a second time period. For example, as the electrochemical actuator 102 is actuated, the actuator 102 can be displaced in a direction toward the fluid source 104 and apply a force to the transfer structure 130. This force will in turn be transferred to the fluid source 104 to pump the fluid out of the fluid source 104, through the fluid communicator 106, and into the target 108. In alternative embodiments, the delivery system 100 may not include a second transfer structure 130 and instead the actuator 102 can act directly on the fluid source 104.

The fluid communicator 106 can be actuated with the actuation of the spring-based actuator 118 and/or the electrochemical actuator 102, whichever is actuated first in a particular embodiment. Activation of the fluid communicator 106 can include, for example, insertion of the fluid communicator 106 into the patient's body. Alternatively, the fluid communicator 106 can be actuated prior to actuation of the spring-based actuator 118 and/or the electrochemical actuator 102. For example, the fluid communicator 106 can be actuated using an insertion mechanism that is separate from the delivery device 100 or a mechanism that is incorporated within the delivery device 100. Example embodiments illustrating various configurations for actuation of a fluid communicator are also described in the '771 patent.

Having described above various general principles, several exemplary embodiments of these concepts are now described. These embodiments are only examples, and many other configurations of a delivery system and/or the various components of a delivery system, are contemplated.

FIGS. 2A and 2B are schematic illustrations of an embodiment of an electrochemical actuator 202 that can be used in a delivery device as described herein. As shown, in this embodiment, the electrochemical actuator 202 can include a positive electrode 210, a negative electrode 212, and an electrolyte 214. These components can form an electrochemical cell that can initially be discharged and then charged before use, or can be initially charged, as shown in FIG. 2A. The positive electrode 210 can be configured to expand or displace in the presence of the electrolyte 214. When a circuit between the electrodes 210, 212 is closed, current can travel from the positive electrode 210 to the negative electrode 212. The positive electrode 210 can then experience a change in volume or shape, resulting in longitudinal displacement of at least a portion of the positive electrode 210, as shown in FIG. 2B. For example, the actuator 202 can have an overall height $h_1$ when it is charged (prior to actuation), as shown in FIG. 2A, and an overall height of $h_2$ when it is discharged or actuated, such that the actuator 202 has a displacement or stroke that is equal to $h_2-h_1$. Said another way, the actuator 202 can have a first end portion 215, a second end portion 219 and a medial portion 217 disposed between the first end portion 215 and the second end portion 219. The actuator prior to actuation (prior to discharge) can be supported on a surface S of the delivery device in which the actuator 202 is disposed, and when the actuator 202 is discharged at least the medial portion 217 can displace (e.g., bend or flex) a non-zero distance from the surface S. The stroke of the actuator 202 can be substantially equal to that non-zero distance. As the actuator 202 is displaced, the actuator 202 can exert a pumping force or pressure on a fluid reservoir (not shown) and/or an associated transfer structure (not shown) coupled thereto. The pumping force or pressure exerted by the actuator 202 can cause a volume of fluid (e.g., a therapeutic agent) to be pumped out of the fluid reservoir. Thus, the electrochemical actuator 202 can be considered a self-powered electrochemical pump.

In this embodiment, the electrochemical actuator 202 has a positive electrode 210 selected to have a lower chemical potential for the working ion when the electrochemical actuator 202 is charged, and is thereby able to spontaneously accept working ions from the negative electrode 212 as the actuator is discharged. In some embodiments, the working ion can include, but is not limited to, the proton or lithium ion. When the working ion is lithium, the positive electrode 210 can include one or more lithium metal oxides including, for example, $LiCoO_2$, $LiFePO_4$, $LiNiO_2$, $LiMn_2O_4$, $LiMnO_2$, $LiMnPO_4$, $Li_4Ti_5O_{12}$, and their modified compositions and solid solutions; oxide compound comprising one or more of titanium oxide, manganese oxide, vanadium oxide, tin oxide, antimony oxide, cobalt oxide, nickel oxide or iron oxide; metal sulfides comprising one or more of $TiSi_2$, $MoSi_2$, $WSi_2$, and their modified compositions and solid solutions; a metal, metal alloy, or intermetallic compound comprising one or more of aluminum, silver, gold, boron, bismuth, gallium, germanium, indium, lead, antimony, silicon, tin, or zinc; a lithium-metal alloy; or carbon comprising one or more of graphite, a carbon fiber structure, a glassy carbon structure, a highly oriented pyrolytic graphite, or a disordered carbon structure. The negative electrode 212 can include, for example, lithium metal, a lithium metal alloy, or any of the preceding compounds listed as positive electrode compounds, provided that such compounds when used as a negative electrode are paired with a positive electrode that is able to spontaneously accept lithium from the negative electrode when the actuator is charged. These are just some examples, as other configurations are also possible.

In some embodiments, the electrochemical actuator can include an anode, a cathode, and a species, such as a lithium ion. In some embodiments, a source of lithium ion is the electrolyte which is made up an organic solvent such as PC, propylene carbonate, GBL, gamma butyl lactone, dioxylane, and others, and an added electrolyte. Some example electrolytes include $LiPF_6$, LiBr, $LiBF_4$. At least one of the electrodes can be an actuating electrode that includes a first portion and a second portion. The portions can have at least one differing characteristic, such that in the presence of a voltage or current, the first portion responds to the species in a different manner than the second portion. For example, the portions can be formed from different materials, or the portions can differ in thickness, dimension, porosity, density, or surface structure, among others. The electrodes can be charged, and when the circuit is closed, current can travel. The species can, intercalate, de-intercalate, alloy with, oxide, reduce, or plate with the first portion to a different extent than the second portion. Due to the first portion responding differently to the species than the second portion, the actuating electrode can experience a change in one or more dimensions, volume, shape, orientation, or position.

Another example of an electrochemical actuator is shown in the embodiment illustrated in FIGS. 3 and 4. As shown in FIG. 3, an electrochemical actuator 302 can include a negative electrode 312 in electrical communication with a positive electrode 310 collectively forming an electrochemical cell. Positive electrode 310 may include a first portion 320 and a second portion 322. In some embodiments, first portion 320 and second portion 322 are formed of different materials. Portions 320 and 322 may also have different electrical potentials. For example, first portion 320 may include a material that can intercalate, de-intercalate, alloy with, oxidize, reduce, or plate a species to a different extent than second portion 322. Second portion 322 may be formed of a material that does not substantially intercalate, de-intercalate, or alloy with, oxidize, reduce, or plate the species. In some embodiments, first portion 320 may be formed of a material including one or more of aluminum, antimony, bismuth, carbon, gallium, silicon, silver, tin, zinc, or other materials which can expand upon intercalation or alloying or compound formation with lithium. In one embodiment, first portion 320 is formed with aluminum, which can expand upon intercalation with lithium. Second portion 322 may be formed of copper, since copper does not substantially intercalate or alloy with lithium. In some instances, second portion 322 may act as a positive electrode current collector, and may extend outside the electrochemical cell, e.g., to form a tab or current lead. In other embodiments, second portion 322 may be joined to a tab or current lead that extends outside the cell. Negative electrode 312 may also include a current collector. Electrochemical actuator 302 may include a separator 323. The separator 323 may be, for example, a porous separator film, such as a glass fiber cloth, or a porous polymer separator. Other types of separators, such as those used in the construction of lithium ion batteries, may also be used. The electrochemical actuator 302 may also include an electrolyte 314, which may be in the form of a liquid, solid, or a gel. The electrolyte may contain an electrochemically active species, such as that used to form the negative electrode. Electrochemical actuator 302 may also include an enclosure 336, such as a polymer packaging, in which negative electrode 312, positive electrode 310 and separator 323 can be disposed.

As illustrated in FIG. 4, the electrochemical cell may have a voltage 333, such that, when a closed circuit is formed between the negative electrode 312 and the positive electrode 310, an electric current may flow between the negative electrode 312 and the positive electrode 310 through the external circuit. If negative electrode 312 is a lithium metal electrode and the electrolyte contains lithium ions, lithium ion current can flow internally from the negative electrode 312 to the positive electrode 310. The intercalation of first portion 320 with lithium can result in a dimensional change, such as a volume expansion. In some instances, this volume expansion may reach at least 25%, at least 50%, at least 75%, at least 100%, at least 150%, at least 200%, at least 250%, or at least 300% compared to the initial volume. High volume expansion may occur, for example, when first portion 320 is saturated with lithium. As first portion 320 increases in volume due to intercalation of lithium, second portion 322 to which first portion 320 may be bonded, may not substantially expand due to minimal or no intercalation of lithium. First portion 320 thus provides a mechanical constraint. This differential strain between the two portions causes positive electrode 310 to undergo bending or flexure. As a result of the dimensional change and displacement of the positive electrode 310, electrochemical actuator 302 can be displaced from a first orientation to a second orientation. This displacement can occur whether the volumetric or dimensional change (e.g., net volume change) of the electrochemical cell, due to the loss of lithium metal from the negative electrode 312 and formation of lithium intercalated compound or lithium alloy at the positive electrode 310, is positive, zero, or negative. In some cases, the actuator displacement may occur with a volumetric or dimensional change (e.g., net volume change) of the electrochemical actuator 302, or portion thereof that is positive. In some cases, the actuator displacement may occur with a volumetric or dimensional change (e.g., net volume change) of the electrochemical actuator 302, or portion thereof that is zero. In some cases, the actuator displacement may occur with a volumetric or dimensional change (e.g., net volume change) of the electrochemical actuator 302, or portion thereof that is negative.

As used herein, "differential strain" between two portions can refer to the difference in response (e.g., actuation) of each individual portion upon application of a voltage or current to the two portions. That is, a system as described herein may include a component including a first portion and a second portion associated with (e.g., may contact, may be integrally connected to) the first portion, wherein, under essentially identical conditions, the first portion may undergo a volumetric or dimensional change and the second portion does not undergo a volumetric or dimensional change, producing strain between the first and second portions. The differential strain may cause the component, or a portion thereof, to be displaced from a first orientation to a second orientation. In some embodiments, the differential strain may be produced by differential intercalation, de-intercalation, alloying, oxidation, reduction, or plating of a species with one or more portions of the actuator system.

For example, the differential intercalation, de-intercalation, alloying, oxidation, reduction, or plating of first portion 320 relative to second portion 322 can be accomplished through several means. In one embodiment, first portion 320 may be formed of a different material than second portion 322, wherein one of the materials substantially intercalates, de-intercalates, alloys with, oxidizes, reduces, or plates a species, while the second portion interacts with the species to a lesser extent. In another embodiment, first portion 320 and second portion 322 may be formed of the same material. For example, first portion 320 and second portion 322 may be formed of the same material and may be substantially dense, or porous, such as a pressed or sintered powder or foam structure. In some cases, to produce a differential strain upon operation of the electrochemical cell, first portion 320 or second portion 322 may have sufficient thickness such that, during operation of the electrochemical cell, a gradient in composition may arise due to limited ion transport, producing a differential strain. In some embodiments, one portion or an area of one portion may be preferentially exposed to the species relative to the second portion or area of the second portion. In other instances, shielding or masking of one portion relative to the other portion can result in lesser or greater intercalation, de-intercalation, or alloying with the masked or shielded portion compared to the non-masked or shielded portion. This may be accomplished, for example, by a surface treatment or a deposited barrier layer, lamination with a barrier layer material, or chemically or thermally treating the surface of the portion to be masked/shielded to either facilitate or inhibit intercalation, de-intercalation, alloying, oxidation, reduction, or plating with the portion. Barrier layers can be formed of any suitable material, which may include polymers, metals, or ceramics. In some cases, the barrier layer can also serve another function in the electrochemical cell, such as being a current collector. The barrier layer may be uniformly deposited onto the surface in some embodiments. In other cases, the barrier layer may form a gradient in composition and/or dimension such that only certain portions of the surface preferentially facilitate or inhibit intercalation, de-intercalation, alloying, oxidation, reduction, or plating of the surface. Linear, step, exponential, and other gradients are possible. In some embodiments a variation in the porosity across first portion 320 or second portion 322, including the preparation of a dense surface layer, may be used to assist in the creation of an ion concentration gradient and differential strain. Other methods of interaction of a species with a first portion to a different extent so as to induce a differential strain between the first and second portions can also be used. In some embodiments, the flexure or bending of an electrode is used to exert a force or to carry out a displacement that accomplishes useful function.

In some embodiments, the electrical circuit can include electrical contacts (not shown) that can open or close the electrical circuit. For example, when the electrical contacts are in communication with each other, the electrical circuit will be closed (as shown in FIG. 4) and when they are not in contact with each other, the electrical circuit can be opened or broken, as shown in FIG. 3.

The discharge of the electrochemical actuator can be relatively proportional to the current traveling through the electrical circuit (i.e., the electrical resistance of the resistor). Because the electrical resistance of the resistor can be relatively constant, the electrochemical actuator can discharge at a relatively constant rate. Thus, the discharge of the electrochemical actuator, and thus the displacement of the electrochemical actuator can be relatively linear with the passage of time.

In some embodiments, an electrical circuit can be used that includes a variable resistor. By varying the resistance, the discharge rate of the electrochemical actuator and the corresponding displacement of the electrochemical actuator can be varied, which in turn can vary the fluid flow rate from the fluid source. An example of such an embodiment is described in the '771 patent. In some embodiments, an electrical circuit can be used that uses a switch to open or close the electrical circuit. When the switch is closed, the electrochemical actuator can discharge and when the switch is opened, the electrochemical actuator can be prevented from discharging. An example of such an embodiment is described in the '771 patent incorporated by reference above.

Figure 6:
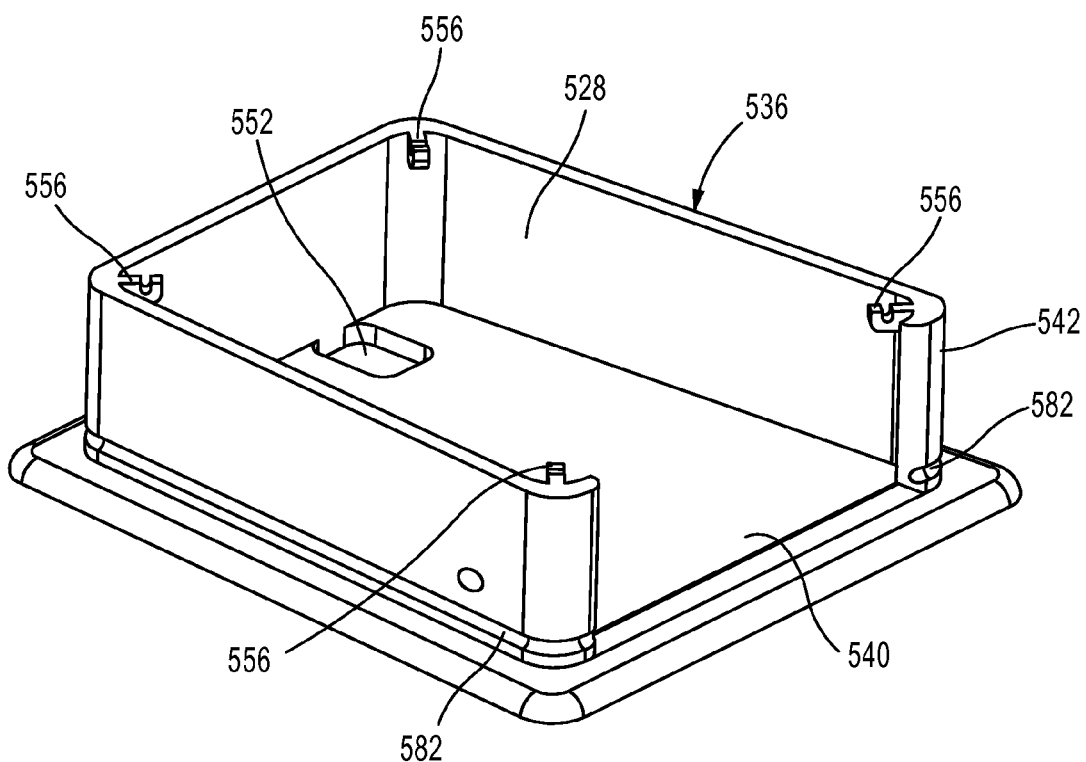
FIG. 6 is a front perspective view of a portion of the delivery device of FIG. 5.

FIGS. 5-21 illustrate a delivery device according to an embodiment. A delivery device 500 includes a housing 526, a first transfer structure 516, a spring-based actuator 518 and a cartridge assembly 532 configured to be received within an interior region 528 (see, e.g., FIG. 6) defined by the housing 526. The cartridge assembly 532 includes a cartridge housing 534, an electrochemical actuator 502, a second transfer structure 530 and a fluid source 504 (see, e.g., FIG. 14). An activation mechanism 574 is also provided as described in more detail below.

The housing 526 includes a base member 536 (see e.g., FIG. 6) and a cover member 538 (see e.g., FIG. 7) that collectively define the interior region 528 when coupled together. The base member 536 includes a floor 540 and upper walls 542. The floor 540 of the base member 536 defines a fluid communicator access opening 552. The cover member 538 is configured to be placed over the upper walls 542 of the base member 536. For example, the cover member 538 defines a lower opening 544 (see e.g., FIG. 7) configured to receive the base member 536.

Figure 8A:
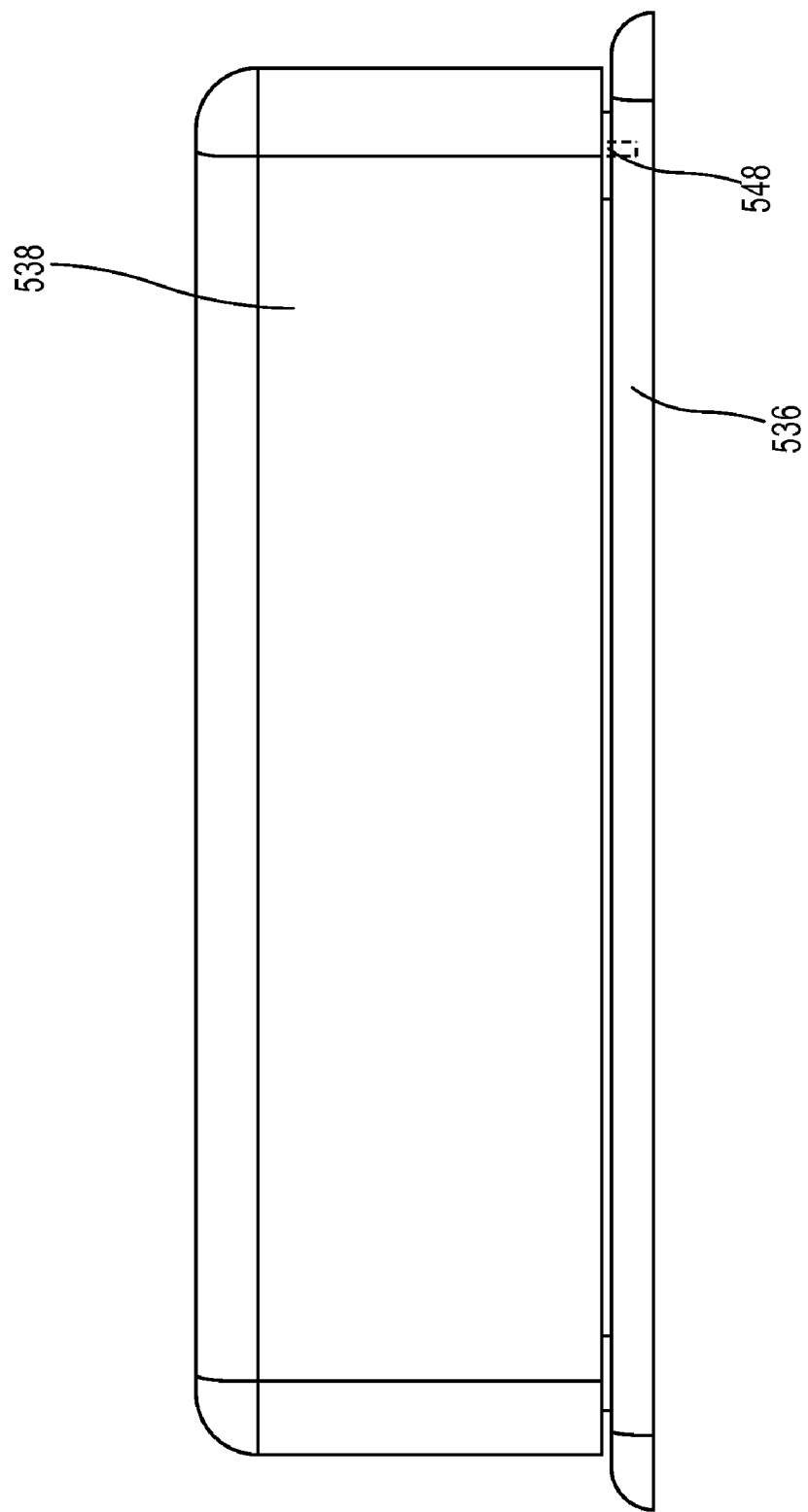
FIG. 8A is a side view of the delivery device of FIG. 5.
Figure 8B:
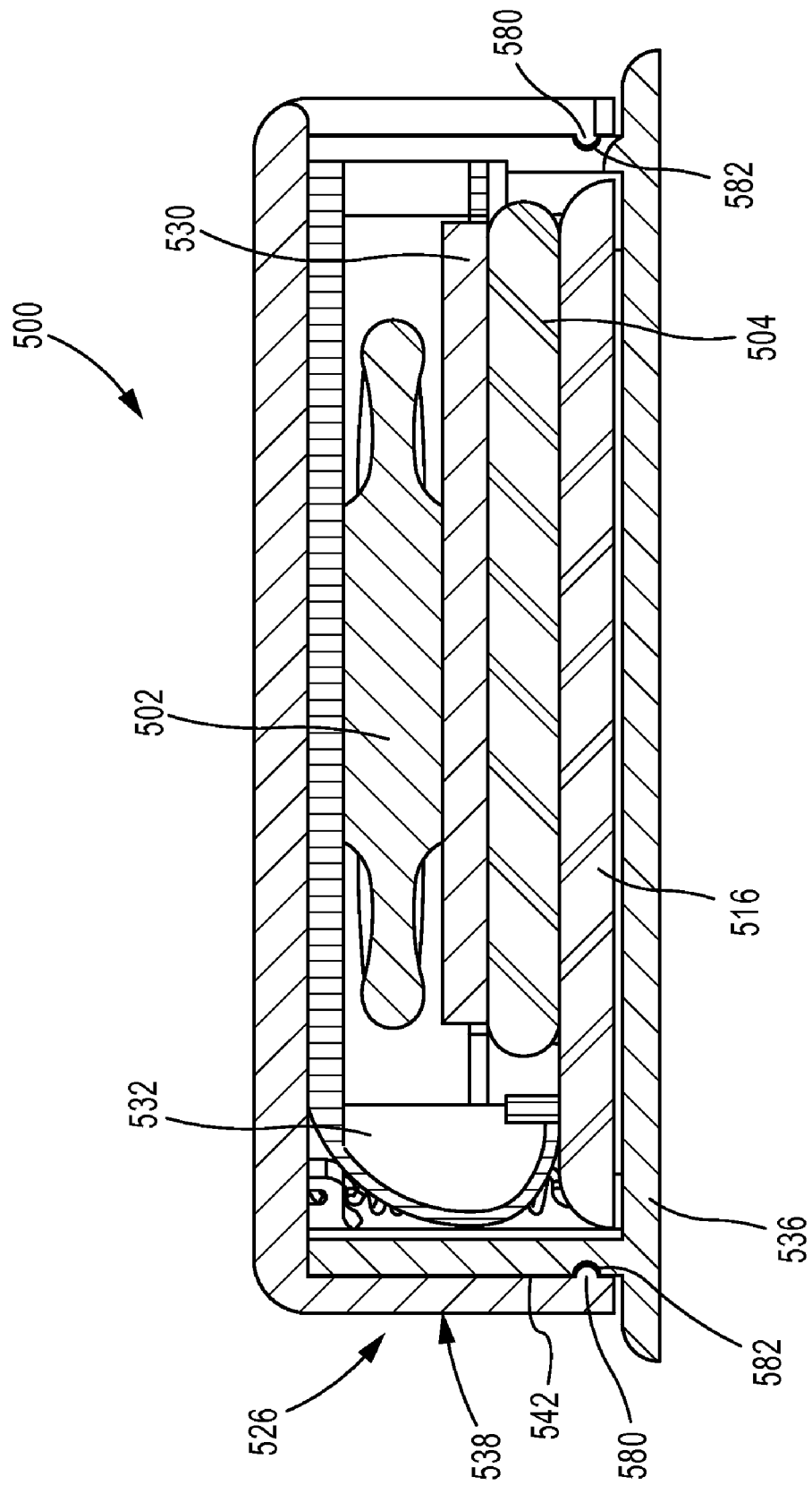
FIG. 8B is a cross-sectional view of the delivery device of FIG. 5, taken along line 5B-5B of FIG. 5.

As shown in FIG. 8B, the cover member 538 includes a protrusion 580 that can be snap-fitted into a corresponding recess 582 in the base member 536. In this embodiment, the protrusion 580 extends about (or substantially about) a lower edge portion of the cover member 538 (see e.g., FIG. 7), and the recess 582 extends about (or substantially about) a lower portion of the upper wall 542 of the base member 536 (see e.g., FIG. 6). A seal member (not shown) can also be provided to seal the internal component of the device. For example, a gasket can be positioned between the base member 536 and the cover member 538 and an additional gasket can be placed on the end of the cartridge so that upon insertion, the device is fully sealed. In some embodiments, the base member 536 and cover member 538 can be coupled together with other types of mechanical attachments, which can be a fixed or removable attachment. For examples tabs or clips that interlock between the base member 536 and cover member 538 can be used. In some embodiments, the base member 536 and cover member 538 can be bonded together with epoxies/glues or via processes that can establish a permanent bond.

The cover member 538 of the housing 526 and the base member 536 of the housing 526 can be coupled together, for example, with adhesive, bonding, mechanical fasteners, or other known coupling methods. In some embodiments, a snap-fit coupling can be used. The cover member 538 can optionally include a guide pin 548 (shown in FIGS. 7 and 8A) configured to be received in an opening (not shown) defined in the base member 536 that can be used to help align the cover member 538 to the base member 536. The cover member 538 also defines a front opening 546 as shown, for example, in FIG. 7. The cartridge assembly 532 (shown e.g., in FIG. 14) can be inserted through the opening 546 and into the interior region 528 of the housing 526.

Figure 9:
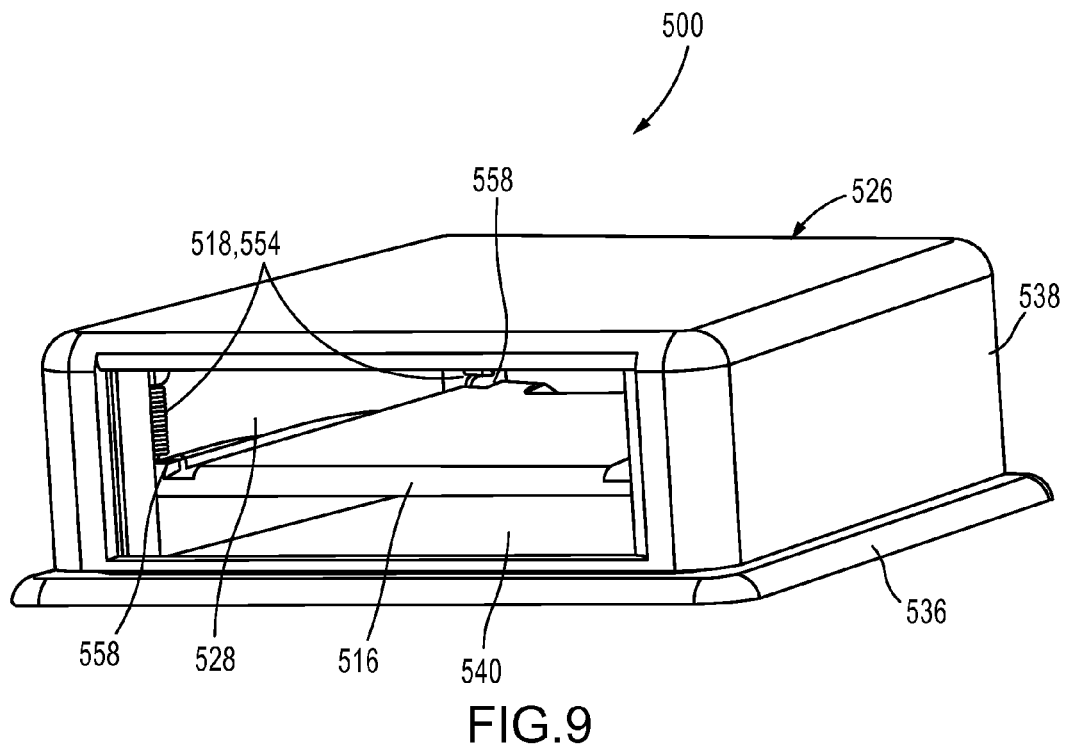
FIG. 9 is a front perspective view of a portion of the delivery device of FIG. 5 showing the spring actuator in a biased natural state.
Figure 10:
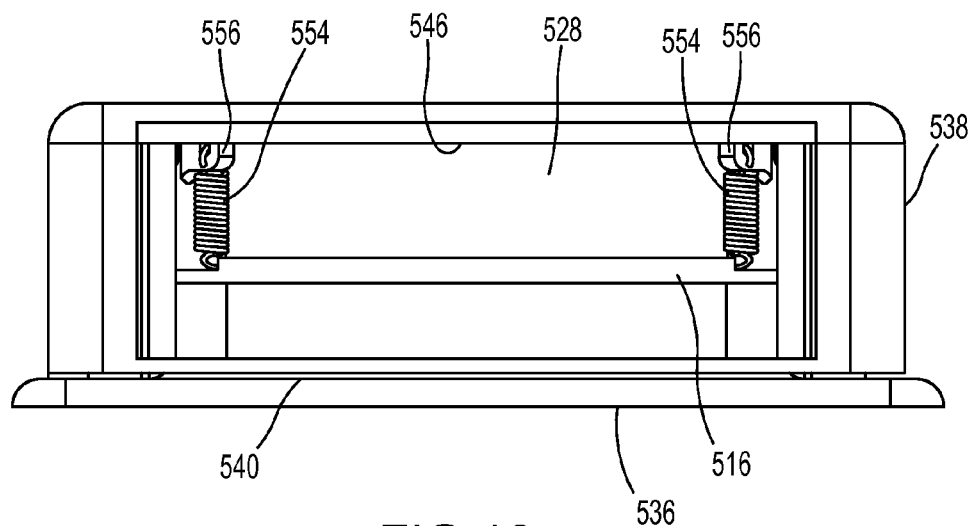
FIG. 10 is a front view of the portion of the delivery device shown in FIG. 9.
Figure 11:
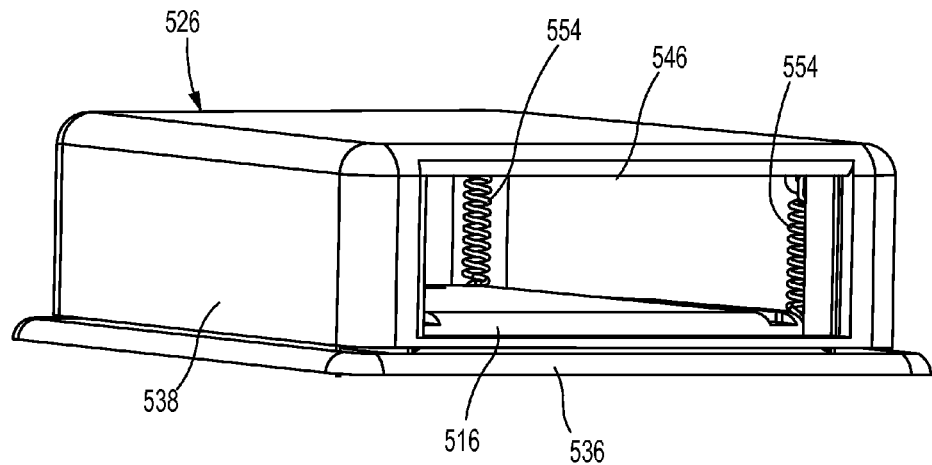
FIG. 11 is a front perspective view of the portion of the delivery device of FIG. 9 showing the spring actuator in a pre-loaded state.
Figure 12:
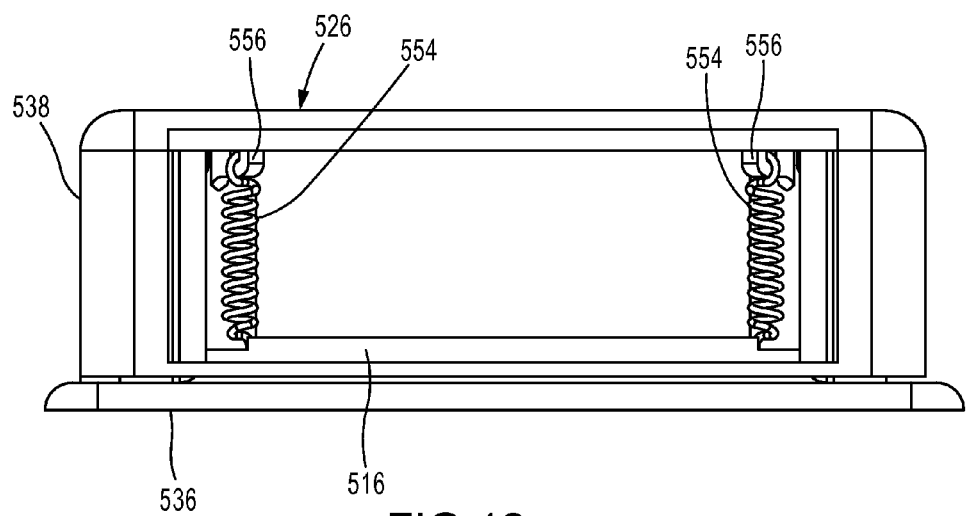
FIG. 12 is a front view of the portion of the delivery device shown in FIG. 11.
Figure 13:
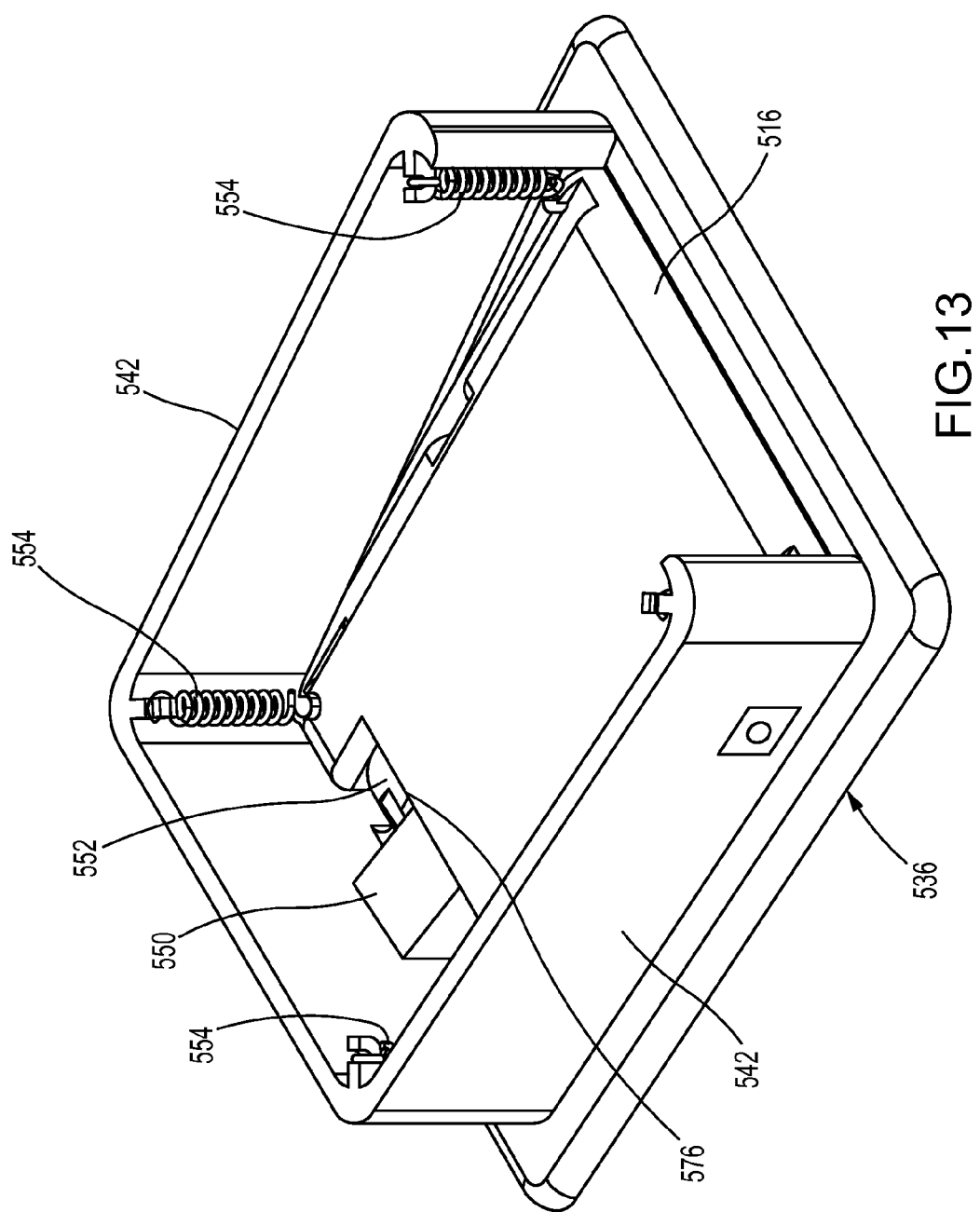
FIG. 13 is a front perspective view of a portion of the delivery device of FIG. 5 shown with the spring actuator in a pre-loaded state.

FIGS. 9 and 10 illustrate the delivery device 500 without the cartridge assembly 532 disposed within the housing 526. FIG. 9 is a front perspective view and FIG. 10 is a front view. The spring-based actuator 518 includes four extension springs 554, one disposed in each corner of the housing 526 (only two are visible in FIGS. 9 and 10). The springs 554 are coupled on one end to the base member 536 of the housing 526 at mounting supports 556 as shown, for example, in FIG. 10 (see also FIG. 6). The springs 554 are coupled on an opposite end to the transfer structure 516 at similar mounting supports 558 (see e.g., FIG. 18). As shown in FIGS. 9 and 10, prior to the cartridge assembly 532 being inserted into the housing 526, the springs 554 are in an unbiased or relaxed state (un-extended), and hold the transfer structure 516 elevated at a spaced distance from the floor 540 of the base member 536. The cartridge assembly 532 can be inserted through the opening 546 and into the housing 526 above the transfer structure 516. As the cartridge assembly 532 is being inserted, the transfer structure 516 is pushed downward, and the springs 554 are moved to an extended state, as shown in FIGS. 11-13. For illustration purposes, FIGS. 11-13 illustrate the movement or repositioning of the transfer structure 516 and the extension of the springs 554 without the cartridge being shown. FIG. 11 is a front perspective view, FIG. 12 is a front view and FIG. 13 is a front perspective view with the cover member 536 also removed for illustration purposes.

Also shown in FIG. 13, the transfer structure 516 defines a cut-out 576 (see also FIG. 18) to provide clearance for an insertion mechanism 550. The insertion mechanism 550 can be disposed within the interior region 528 of the housing 526. The insertion mechanism 550 can be configured to insert a fluid communicator (not shown) through the opening 552 in the base member 536 of the housing 526 and into a target (e.g., a patient's body). The insertion mechanism 550 can also be configured to puncture the fluid source 504 and provide fluid communication between the fluid source 504 and the fluid communicator.

Figure 14:
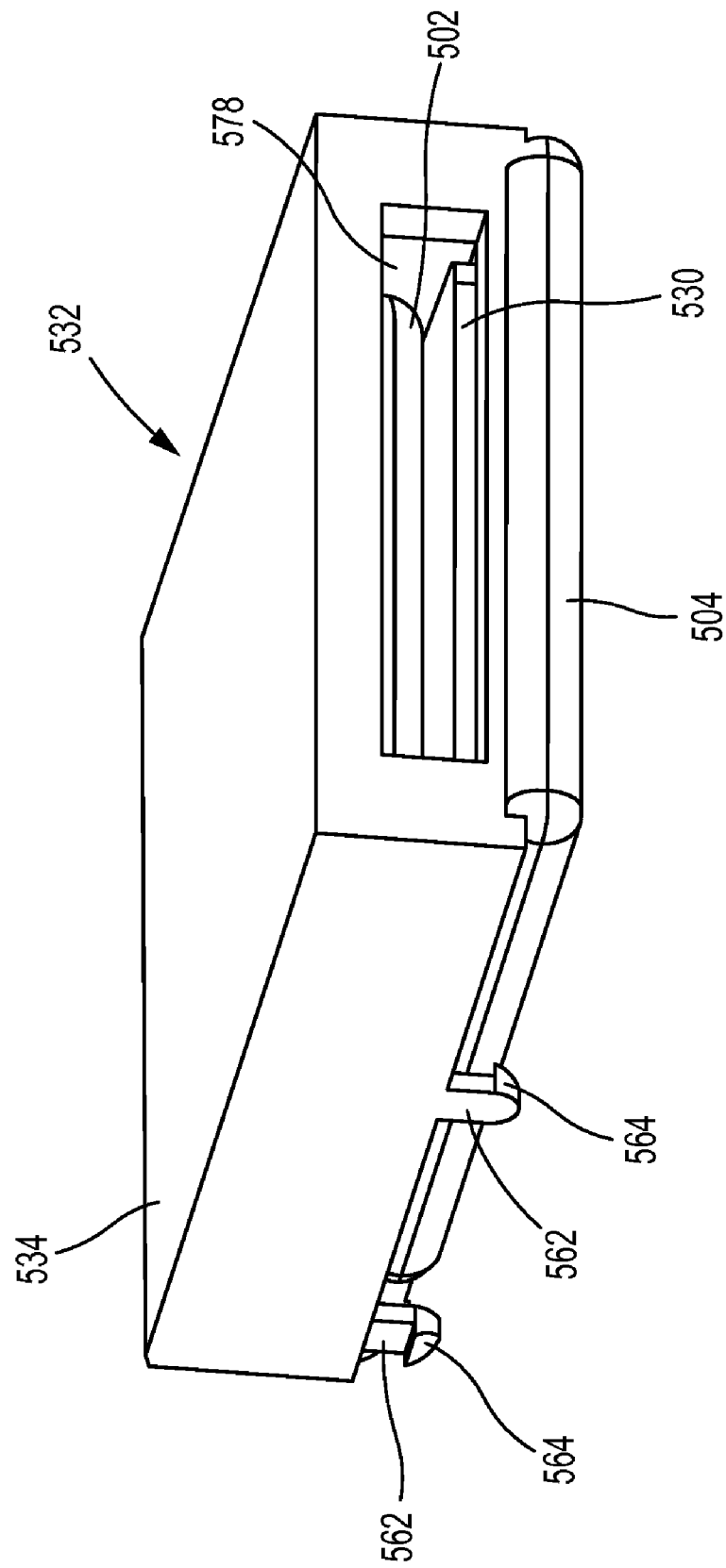
FIG. 14 is a front perspective view of a cartridge assembly of the delivery device of FIG. 5.
Figure 15:
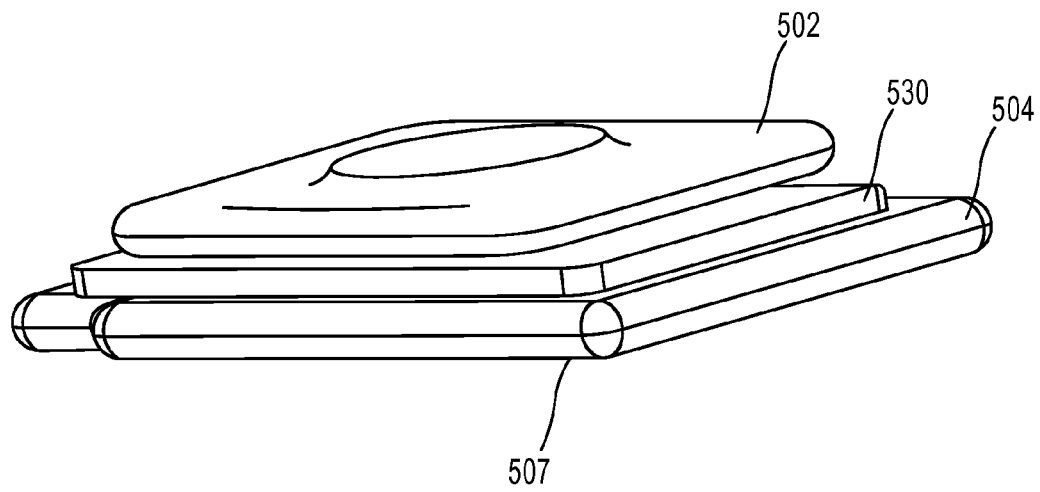
FIG. 15 is a front perspective view of a portion of the cartridge assembly of FIG. 14.
Figure 16:
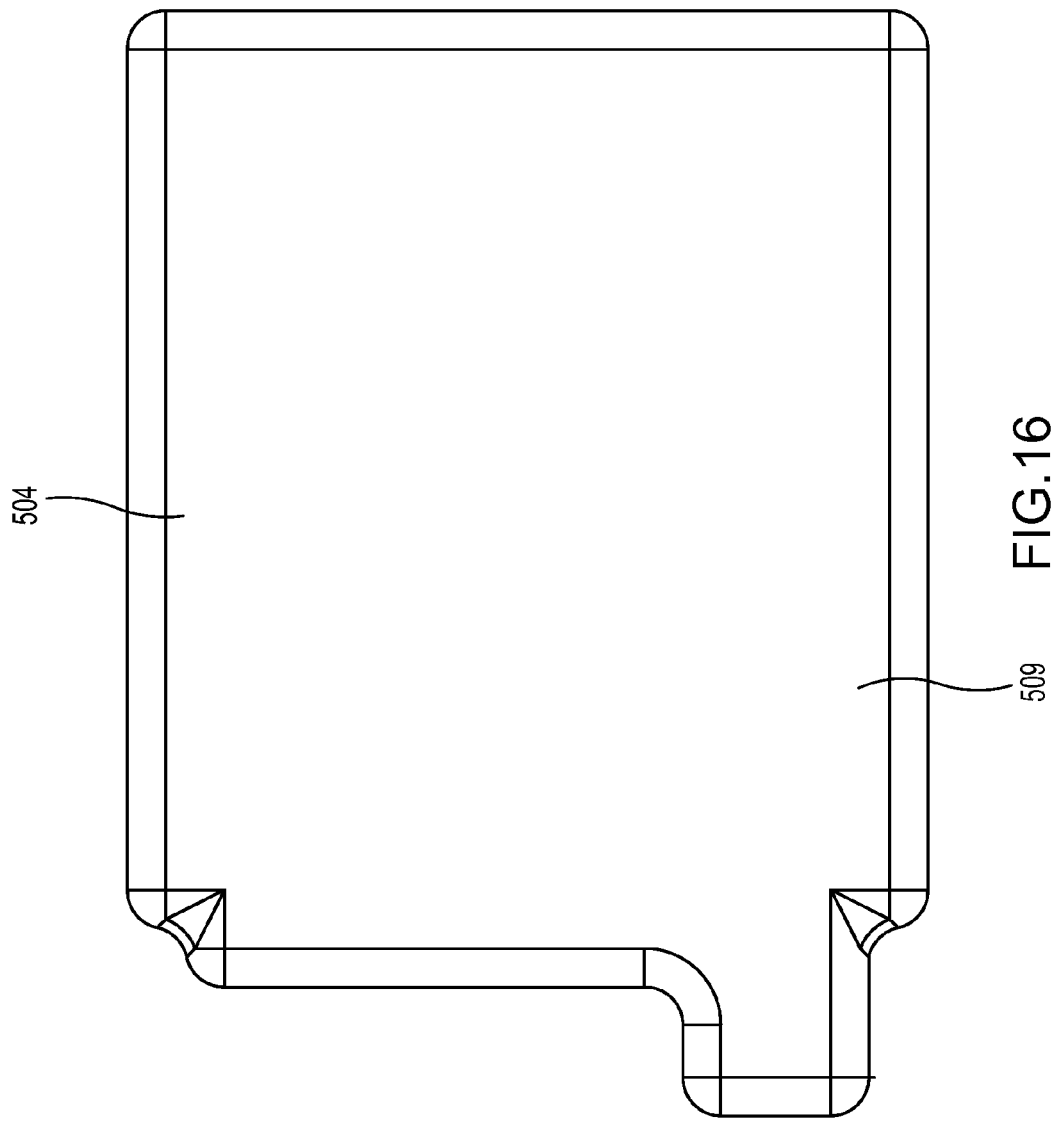
FIG. 16 is a top view of the fluid reservoir of the delivery device of FIG. 5.

As stated above, and as shown in FIGS. 14 and 15, the cartridge assembly 532 includes the cartridge housing 534, the electrochemical actuator 502, the transfer structure 530 and the fluid source 504 containing a volume of fluid to be delivered to a target (e.g., patient). The electrochemical actuator 502 can be configured to function in the same or similar manner as described above for other embodiments. FIG. 15 illustrates the transfer structure 530 disposed between the electrochemical actuator 502 and the fluid source 504 (without the cartridge housing 532), and FIG. 16 is a top view of the fluid source 504.

Figure 17:
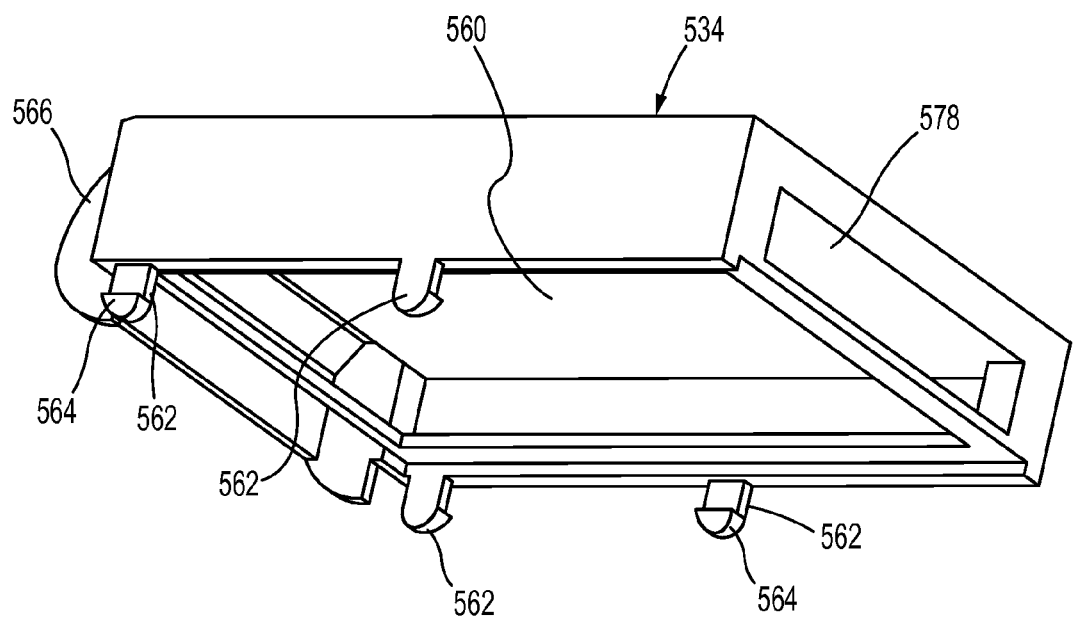
FIG. 17 is a bottom perspective view of a portion of the cartridge assembly of FIG. 14.
Figure 18:
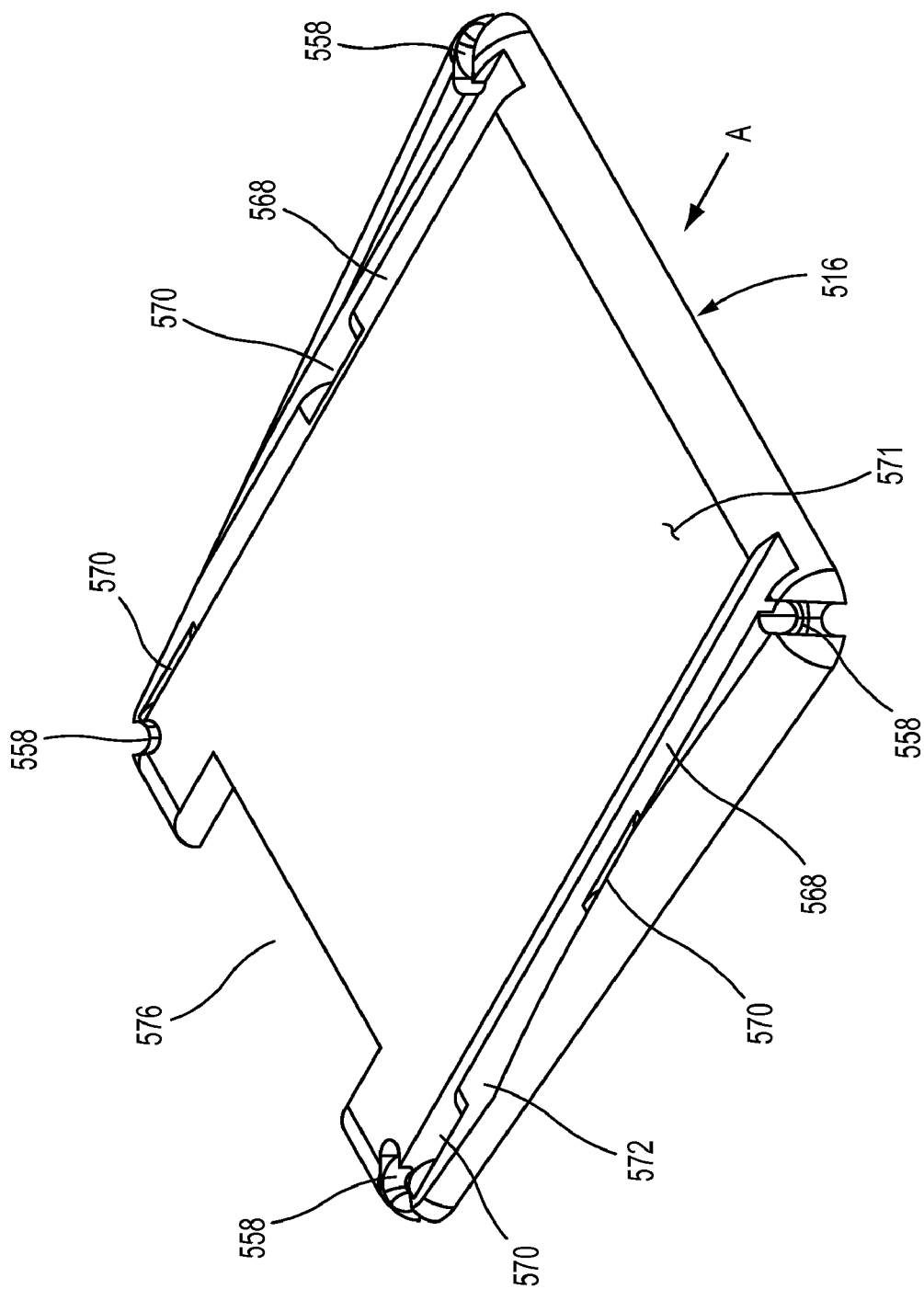
FIG. 18 is a front perspective view of a transfer structure of the delivery device of FIG. 5.
Figure 19:
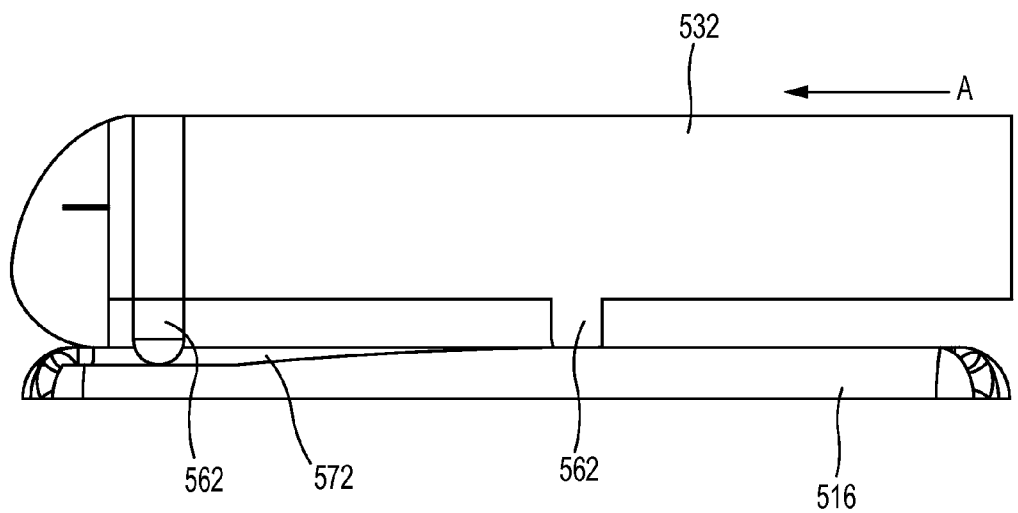
FIG. 19 is a side view of a portion of the delivery device of FIG. 5.

As shown in FIG. 17, the cartridge housing 534 defines a front access opening 578 and an opening 560 defined in a bottom face of the cartridge housing 534. The cartridge housing 534 also includes legs 562 with hooks 564, and a rear hub portion 566. The legs 562 are used to couple the cartridge assembly 532 to the transfer structure 516 when the cartridge assembly 532 is inserted into the housing 526. The hooks provide a snap-fit coupling between the cartridge assembly 532 and the transfer structure 516. As shown in FIG. 18, the transfer structure 516 defines tracks 568 and slots 570 in which the legs 562 can be received when inserting the cartridge assembly 532 into the interior region 528 of the housing 526. The tracks 568 also include ramped portions 572 to help facilitate insertion of the cartridge assembly 532. Specifically, as the cartridge assembly 532 is being inserted in the direction of arrow A (shown in FIGS. 18 and 19), the legs 562 of the cartridge housing 534 can slide within the tracks 568 until the cartridge assembly 532 is positioned above the slots 570. This aligns the cartridge assembly 532 to properly move the transfer structure 516 downward. As the cartridge assembly 532 is moved downward, it pushes the transfer structure 516 into the housing 526 to a pre-actuation position, which in turn extends the springs 554 of the actuator 518 from their natural state (un-extended) to an extended state. This places the springs 554 in a pre-loaded position, and places a bottom surface 507 of the fluid source 504 (see, e.g., FIG. 15) in contact with a top surface 571 of the transfer structure 516. The transfer structure 516 is then pulled upward by the springs 554 such that the cartridge legs 562 are inserted into the slots 570 of the transfer structure 516, and the hooks 562 are snap-fitted to the transfer structure 516.

Figure 20:
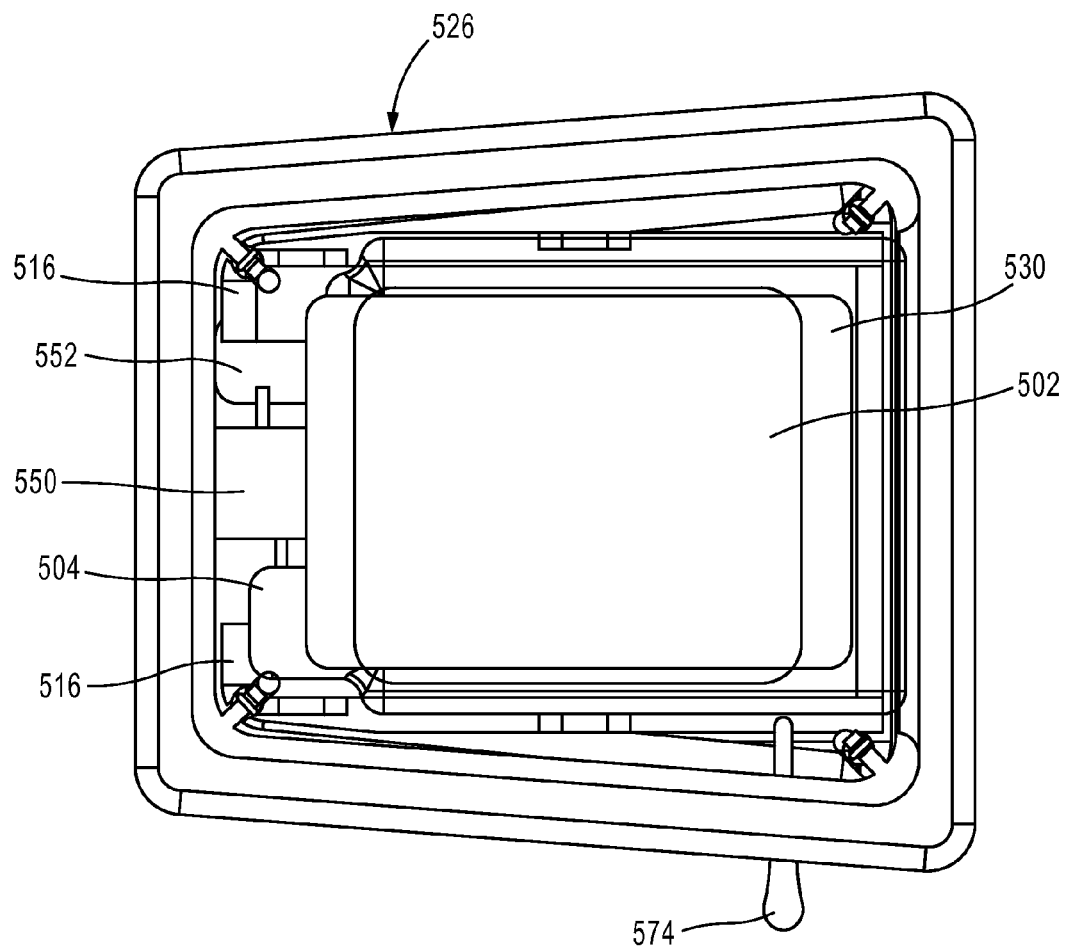
FIG. 20 is a top view of a portion of the delivery device of FIG. 5.

FIG. 20 is a top view of the delivery device 500 with the cover member 536 and cartridge housing 534 removed for illustration purposes. As shown in FIG. 20, the fluid source 504 is disposed such that it can contact the insertion mechanism 550. With the cartridge assembly 532 coupled to the transfer structure 516, the activation mechanism 574 (see also FIG. 5) can be moved to a hold position to maintain the transfer structure 516 in its pre-actuation position and the delivery device 500 in a ready position. The activation mechanism 574 can be, for example, a pull-tab with pin member. Other types of mechanisms, such as a button, switch, electrical activation mechanism, etc., can alternatively be used. In some embodiments, a separate mechanism can be used to move the transfer structure 516 to its pre-actuation position. For example, a delivery device can include a mechanism configured to move the transfer structure 516 to its pre-actuation position prior to the cartridge assembly 532 being inserted into the housing 526. In some embodiments, a separate device external to the delivery device can be used to move the transfer structure 516 to its pre-actuation position.

Figure 21:
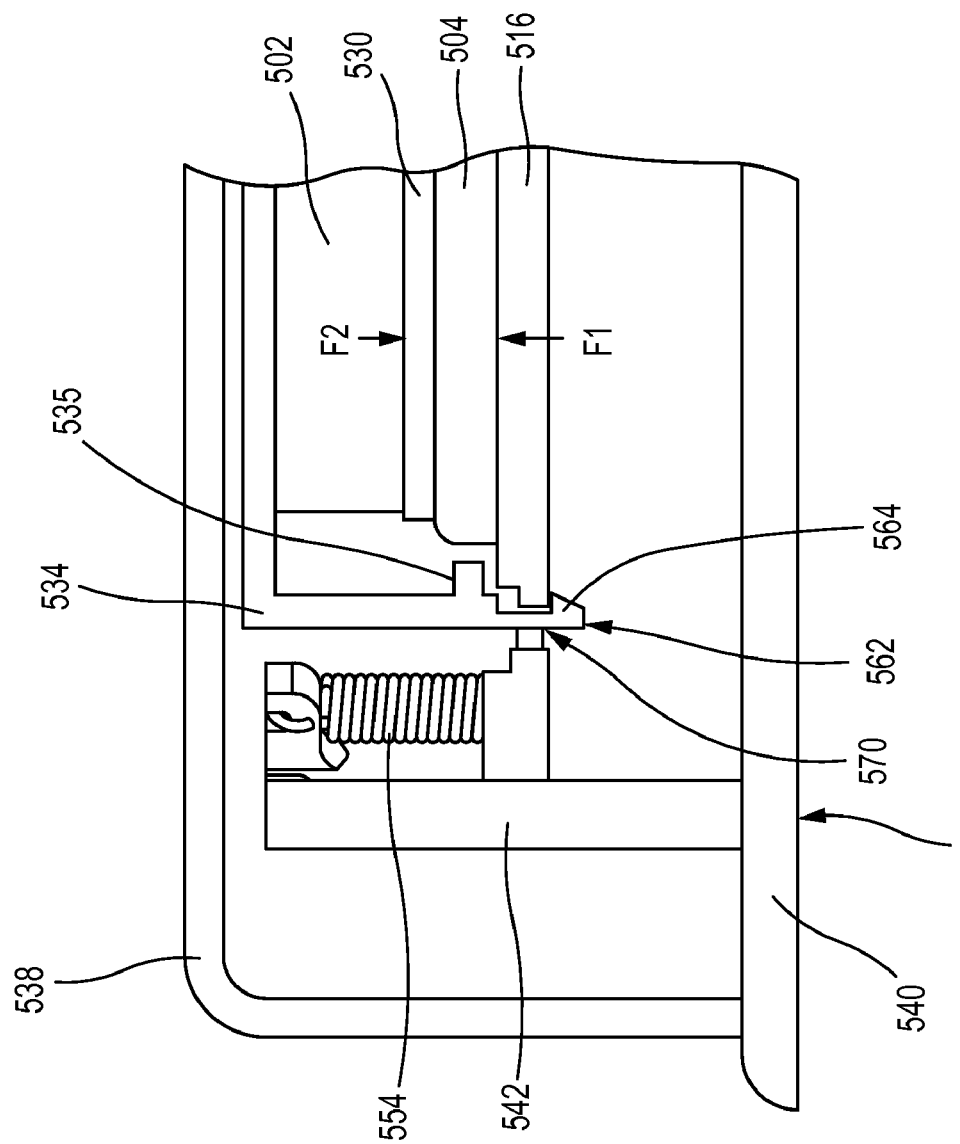
FIG. 21 is a partial cut-away view of a portion of the delivery device of FIG. 5.

In use, with the delivery device 500 in the ready position, the delivery device 500 can be placed in contact with a target (e.g. placed on the surface of a patient's body), such that the opening 552 in the base member 536 is disposed adjacent to a desired injection site. The delivery device 500 can be activated by moving the activation mechanism 574 to a start position, releasing the transfer structure 516 from its pre-actuation position. This starts a first actuation of the delivery device 500. Specifically, when the delivery device 500 is activated, the springs 554 of the actuator 518 will be free to move upward back to their biased natural or relaxed state (un-extended), pulling the transfer structure 516 upward with them. As the transfer structure 516 is moved upward, it exerts a first force F1 (see the partial cut-away view of FIG. 21) on the bottom surface 507 of fluid source 504, thereby compressing the fluid source 504 and causing a first volume of fluid to be expelled out of the fluid source 504 (through a fluid communicator) and into the target (e.g., patient). As shown in FIG. 21, when the transfer structure 516 is moved upward by the pulling force of the springs 554, the cartridge assembly 532 is also moved upward due to its attachment to the transfer structure 516. The actuation of the spring-based actuator 518 (e.g., springs 554) can continue, for example, until the transfer structure 516 reaches a mechanical stop 535 within the cartridge housing 534. As such, the mechanical stop 535 can be positioned within the cartridge assembly 534 to help limit the amount of fluid (e.g., to the first volume) expelled from the fluid source 504 during actuation of the spring-based actuator 518. The travel of the cartridge assembly 532 is also limited by the height of the inside of the cover member 538. The coupling of the legs 562 of the cartridge housing 534 to the transfer structure 516 limits the transfer structure 516 from reversing its motion (e.g., moving downward after the spring-based actuator is actuated). Specifically, the hooks 564 of the legs 562 limit the travel of the transfer structure 516 in the downward direction. Furthermore, because the springs 554 are in their natural, un-extended, state, the springs also help to limit travel of the transfer structure 516 in the downward direction (e.g., towards its original position).

When the spring-based actuator 518 has completed its actuation, the electrochemical actuator 502 can then be actuated to provide a second phase of delivery of a volume of fluid from the fluid source 504. Specifically, when the transfer structure 516 reaches the mechanical stop 535, it can also activate a trigger (not shown) associated with the electrochemical actuator 502. For example, such a trigger can complete the electric circuit (as described above) and cause the electrochemical actuator 502 to start discharging. As the electrochemical actuator 502 discharges, it will displace and exert a second force F2 (see FIG. 21) on a top surface 509 (see e.g., FIG. 16) of the fluid source 504, thereby compressing the fluid source 504 and causing a second volume of fluid within the fluid source 504 to be expelled into the target (e.g., patient). As stated above, and as shown in FIG. 21, the legs 562 of the cartridge housing 534 that are secured within the slots 570 of the transfer structure 516 limit the movement of the transfer structure 516 to prevent it from being forced downward away from the fluid source 504 as the electrochemical actuator 502 is being actuated. Specifically, the hooks 564 limit the downward motion of the transfer structure 516 as the electrochemical actuator 502 is actuated.

In some embodiments, the insertion mechanism 550 can be activated upon insertion of the cartridge assembly 532. For example, as the cartridge assembly 532 is being inserted, a trigger (not shown) on the insertion mechanism 550 can be activated to puncture the fluid source 504 and insert a fluid communicator (not shown) through the opening 552 and into the target (e.g., patient). In some embodiments, the insertion mechanism 550 can be actuated when the delivery device 500 is actuated. For example, the activation mechanism 574 can also be configured to activate the insertion mechanism 550 when activated to start the actuators as described above. In some embodiments, a separate button, tab, switch, etc. (not shown) can be used to cause the insertion mechanism 550 to puncture the fluid source 550, insert a fluid communicator, or both. In some embodiments, the puncturing of the fluid source and insertion of the fluid communicator can be simultaneous or sequential. In addition, although not shown, in some embodiments, an insertion mechanism can alternatively be provided in the cartridge assembly 532. For example, an insertion mechanism can be disposed within an interior region defined by the rear hub portion 566 of the cartridge housing 534.

FIGS. 22A and 22B are schematic illustrations of the forces exerted by the spring-based actuator 518 and the electrochemical actuator 502 in the above-described embodiment. As shown in FIG. 22A, the spring-based actuator 518 exerts a first force F1 in a first direction. The force F1 is a pulling force (from the extension springs 554) applied to the transfer structure 516, which in turns transfers to the fluid source 504. FIG. 22B illustrates a second force F2 in a second direction exerted by the electrochemical actuator 502 to the transfer structure 530, which in turn is transferred to the fluid source 504.

The electrochemical actuator 502 can be configured to be actuated for a specific time period after the actuation of the spring-based actuator 518 to deliver a desired volume of fluid to the target. For example, the electrochemical actuator 502 can be configured to correspond to the particular size of the fluid source 504 and the volume of fluid contained therein such that the activation will be complete when the fluid in the fluid source 504 has been completely expelled from the fluid source 504. The rate of actuation of the spring-based actuator 516 can be faster than the rate of activation of the electrochemical actuator 502. Thus, the delivery device 500 can be actuated to deliver a volume of fluid from the fluid source 504 at a first rate during a first time period using the spring-based actuator 518, and a second volume of fluid at a second rate during a second time period using the electrochemical actuator 502.

In alternative embodiments, a delivery device as described herein can be configured with alternative dispensing scenarios. For example, the delivery device can be configured such that the electrochemical actuator is activated first, and the spring-based actuator is actuated second by activating a button, switch, pull-tab, electrical activation mechanism, etc. at a desired time after the electrochemical actuator has been activated. In some embodiments, activation of the electrochemical actuator and the spring-based actuator can overlap for some or all of their respective activation durations. In some embodiments, additional controls can be included to release the spring-based actuator 518 (i.e., springs 554) at a desired time either before after or during the activation of the electrochemical actuator 502. For example, a mechanical and/or electrical mechanism (e.g., button, switch) can be used.

In some embodiments, compression springs can be used instead of extension springs. For example, in such an embodiment, the compression springs can apply a pushing force on the transfer structure rather than a pulling force. FIG. 23 is a schematic illustration of the forces associated with such an embodiment. As shown in FIG. 23, a spring-based actuator 618 including compression springs can exert a first force F1 in a first direction. In this example, the force F1 is a pushing force applied to a transfer structure 616, which in turns transfers to a fluid source 604. A second force F2 in a second direction can be exerted by an electrochemical actuator 602 to a transfer structure 630, which in turn is transferred to the fluid source 604. The order of actuation can be reversed as described herein.

The spring-based actuators described herein can be selected based in part, on two extreme points of operation: a starting point and an end point. For example, for a delivery device such as delivery device 500 having a spring-based actuator 518 using extension springs configured to be activated first, and an electrochemical actuator 502 configured to be activated second, the starting point is where the springs are in their most extended state. The end point can be an intermediate extension of the springs that provides the necessary force to still push fluid out of the fluid source 504 at the point where the electrochemical actuator starts. If compression springs are used, the starting point is when the springs are in a most compressed state and an end point can be an intermediate compression of the springs that provides the necessary force to still push fluid out of the fluid source at the point where the electrochemical actuator starts. Certain types of springs (e.g., discs) also have relatively constant profiles, which can provide further benefits as they can provide more efficient use of volume.

Although delivery device 500 was described as having one electrochemical actuator, in alternative embodiments, more than one electrochemical actuator can be included. For example, two (or more) electrochemical actuators can be provided. The electrochemical actuators can be configured to be actuated simultaneously or sequentially to increase the amount of force and/or displacement applied to the fluid source. For example, a spring-based actuator can be actuated, a first electrochemical actuator can be actuated, and a second electrochemical actuator can be actuated, in any order and/or combination.

Figure 24:
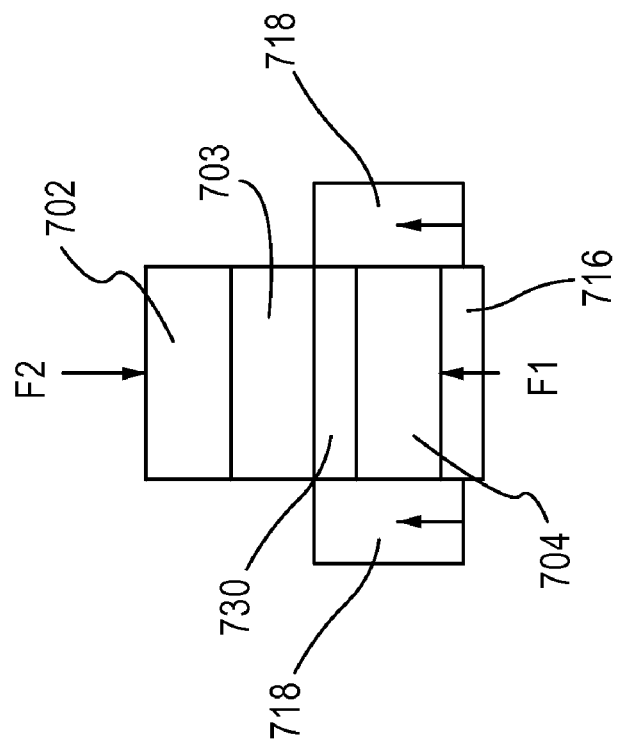
FIG. 24 is a schematic illustration of an embodiment of a delivery device showing the forces exerted by a first actuator and the forces exerted by a second actuator.

FIG. 24 is a schematic illustration of an embodiment of a delivery device having two electrochemical actuators 702 and 703, and a spring-based actuator 718 and the forces associated with such an embodiment. As shown in FIG. 24, the spring-based actuator 718 can exert a first force F1 in a first direction applied to a transfer structure 716, which in turns transfers to a fluid source 704. A second force F2 in a second direction can be exerted by the two electrochemical actuators 702 and 703 to a transfer structure 730, which in turn is transferred to the fluid source 704. The order of actuation can be reversed as described herein.

Figure 25:
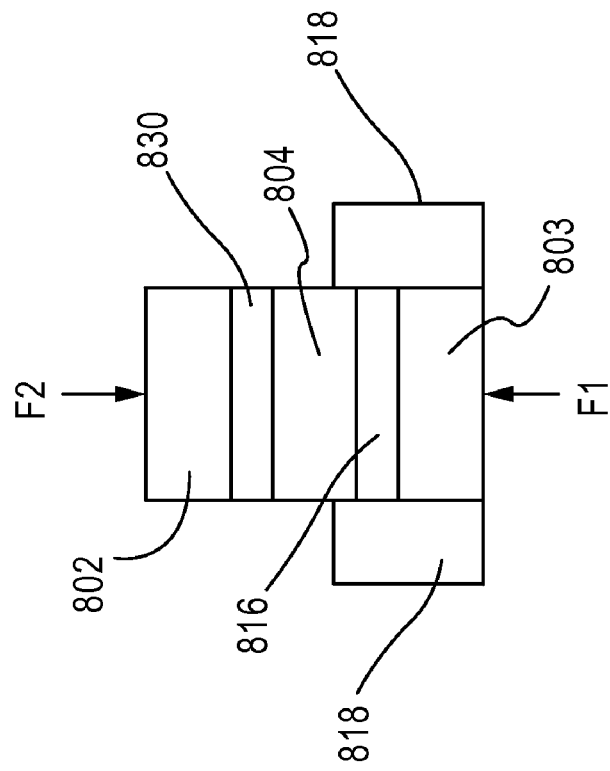
FIG. 25 is a schematic illustration of an embodiment of a delivery device showing the forces exerted by a first actuator and the forces exerted by a second actuator.

FIG. 25 is a schematic illustration of another embodiment of a delivery device having two electrochemical actuators 802 and 803, and a spring-based actuator 818 and the forces associated with such an embodiment. In this example embodiment, the spring-based actuator 818 can be used in conjunction with one of the electrochemical actuators to exert a force in one direction and the other electrochemical actuator can exert a force in a second direction. As shown in FIG. 25, a first force F1 in a first direction is applied by the spring-based actuator 818 together with the electrochemical actuator 803 to a transfer structure 816, which in turns transfers to a fluid source 804. A second force F2 in a second direction can be exerted by the electrochemical actuator 802 to a transfer structure 830, which in turn is transferred to the fluid source 804. The order of actuation can be reversed as described herein.

In some embodiments of a delivery device, a first actuator (e.g., an electrochemical actuator or a mechanical actuator) can be actuated for a first time period and a second actuator (e.g., an electrochemical actuator or a mechanical actuator) can be actuated for a second time period, and the first time period and the second time period can at least partially overlap. For example, the first actuator may be actuated and during its actuation, the second actuator is actuated. In some embodiments, both actuators can be actuated at the same time, but provide different rates of actuation. For example, a first actuator can be configured to actuate at a first rate that is faster than the actuation of the second actuator. Thus, the first actuator and the second actuator can start at the same time, but the second actuator will actuate for a longer duration.

Example strokes and operating forces for an electrochemical actuator can be, for example, in the range of 2 mm-5 mm and 5N-50N respectively. In some embodiments, the stroke and operating force is greater than 5 mm and 50 N, respectively. In some embodiments, the force provided by an extension spring used in a spring-based actuator can be, for example, from 30N-50N at peak extension and down to, for example about 10 N-15 N at mid-stroke of approximately 2 mm-3 mm.

A delivery device (e.g., 100, 500) as described herein may be used to deliver a variety of drugs according to one or more release profiles. For example, the drug may be delivered according to a relatively uniform flow rate, a varied flow rate, a preprogrammed flow rate, a modulated flow rate, in response to conditions sensed by the device, in response to a request or other input from a user or other external source, or combinations thereof. Thus, embodiments of the delivery device may be used to deliver drugs having a short half-life, drugs having a narrow therapeutic window, drugs delivered via on-demand dosing, normally-injected compounds for which other delivery modes such as continuous delivery are desired, drugs requiring titration and precise control, and drugs whose therapeutic effectiveness is improved through modulation delivery or delivery at a non-uniform flow rate. These drugs may already have appropriate existing injectable formulations.

For example, the delivery devices may be useful in a wide variety of therapies. Representative examples include, but are not limited to, opioid narcotics such as fentanyl, remifentanyl, sufentanil, morphine, hydromorphone, oxycodone and salts thereof or other opioids or non-opioids for post-operative pain or for chronic and breakthrough pain; NonSteroidal Antinflamatories (NSAIDs) such as diclofenac, naproxen, ibuprofin, and celecoxib; local anesthetics such as lidocaine, tetracaine, and bupivicaine; dopamine antagonists such as apomorphine, rotigotine, and ropinerole; drugs used for the treatment and/or prevention of allergies such as antihistamines, antileukotrienes, anticholinergics, and immunotherapeutic agents; antispastics such as tizanidine and baclofin; insulin delivery for Type 1 or Type 2 diabetes; leutenizing hormone releasing hormone (LHRH) or follicle stimulating hormone (FSH) for infertility; plasma-derived or recombinant immune globulin or its constituents for the treatment of immunodeficiency (including primary immunodeficiency), autoimmune disorders, neurological and neurodegenerative disorders (including Alzheimer's Disease), and inflammatory diseases; apomorphine or other dopamine agonists for Parkinson's disease; interferon A for chronic hepatitis B, chronic hepatitis C, solid or hematologic malignancies; antibodies for the treatment of cancer; octreotide for acromegaly; ketamine for pain, refractory depression, or neuropathic pain; heparin for post-surgical blood thinning; corticosteroid (e.g., prednisone, hydrocortisone, dexamethasone) for treatment of MS; vitamins such as niacin; Selegiline; and rasagiline. Essentially any peptide, protein, biologic, or oligonucleotide, among others, that is normally delivered by subcutaneous, intramuscular, or intravenous injection or other parenteral routes, may be delivered using embodiments of the devices described herein. In some embodiments, the delivery device can be used to administer a drug combination of two or more different drugs using a single or multiple delivery port and being able to deliver the agents at a fixed ratio or by means enabling the delivery of each agent to be independently modulated. For example, two or more drugs can be administered simultaneously or serially, or a combination (e.g. overlapping) thereof.

In some embodiments, the delivery device may be used to administer ketamine for the treatment of refractory depression or other mood disorders. In some embodiments, ketamine may include either the racemate, single enantiomer (R/S), or the metabolite (wherein S-norketamine may be active). In some embodiments, the delivery devices described herein may be used for administration of Interferon A for the treatment of hepatitis C. In one embodiment, a several hour infusion patch is worn during the day or overnight three times per week, or a continuous delivery system is worn 24 hours per day. Such a delivery device may advantageously replace bolus injection with a slow infusion, reducing side effects and allowing the patient to tolerate higher doses. In other Interferon A therapies, the delivery device may also be used in the treatment of malignant melanoma, renal cell carcinoma, hairy cell leukemia, chronic hepatitis B, condylomata acuminata, follicular (non-Hodgkin's) lymphoma, and AIDS-related Kaposi's sarcoma.

In some embodiments, a delivery device as described herein may be used for administration of apomorphine or other dopamine agonists in the treatment of Parkinson's Disease ("PD"). Currently, a bolus subcutaneous injection of apomorphine may be used to quickly jolt a PD patient out of an "off" state. However, apomorphine has a relatively short half-life and relatively severe side effects, limiting its use. The delivery devices described herein may provide continuous delivery and may dramatically reduce side effects associated with both apomorphine and dopamine fluctuation. In some embodiments, a delivery device as described herein can provide continuous delivery of apomorphine or other dopamine agonist, with, optionally, an adjustable baseline and/or a bolus button for treating an "off" state in the patient. Advantageously, this method of treatment may provide improved dopaminergic levels in the body, such as fewer dyskinetic events, fewer "off" states, less total time in "off" states, less cycling between "on" and "off" states, and reduced need for levodopa; quick recovery from "off" state if it occurs; and reduced or eliminated nausea/vomiting side effect of apomorphine, resulting from slow steady infusion rather than bolus dosing.

In some embodiments, a delivery device as described herein may be used for administration of an analgesic, such as morphine, hydromorphone, fentanyl or other opioids, in the treatment of pain. Advantageously, the delivery device may provide improved comfort in a less cumbersome and/or less invasive technique, such as for post-operative pain management. Particularly, the delivery device may be configured for patient-controlled analgesia.

In some embodiments, all or some of the components of a delivery system can be included in a kit. For example, a kit can include at least a housing (e.g., housing 526) with an actuator and a reservoir (e.g., fluid source 504). The reservoir has a first configuration in which the reservoir is separate from the housing and a second configuration in which at least a portion of the reservoir is received in the housing. Upon actuation, the actuator is configured to exert a force on the reservoir when the reservoir is in its second configuration such that at a volume of the fluid is communicated out of the reservoir. In some embodiments, the reservoir is included in a cartridge assembly. The cartridge assembly is configured to be slidably inserted into an opening in the housing. In some embodiments, when the cartridge assembly is inserted into the housing, the actuator is placed in a pre-loaded position (such as described above with respect to cartridge assembly 532).

The reservoir and/or the cartridge assembly can be maintained separately from the housing and its components within the kit packaging. For example, the reservoir and/or the cartridge assembly can be disposed within a first portion of the kit such that a temperature, humidity, or other environmental factor is controlled or maintained independent of a temperature, humidity, or other environmental factor of a section portion of the kit in which other delivery system components (e.g., the housing) are disposed. For example, the reservoir can be insulated (e.g., by enclosure in an insulated material or compartment). In another example, the reservoir can be disposed in a temperature controlled compartment (e.g., in a refrigerated or heated compartment) within the kit. As such, the kit is contemplated to include a reservoir containing one or more of a variety of temperature-sensitive fluids, whether such fluids are temperature-sensitive based on the fluid medium or a drug, contrast agent, diagnostic agent, or other therapeutic agent included therein. Additionally, because the reservoir and any therapeutic fluid or agent contained therein can be temperature-controlled, the shelf-life of the therapeutic fluid or agent can be extended (or at least not be undesirably shortened). In other words, the reservoir can be packaged within the kit in a manner to limit degradation, deterioration, or reduced efficacy of a drug, contrast agent, diagnostic agent, or other therapeutic agent or fluid contained within the reservoir, such as may otherwise occur in at an undesirable temperature.

In some embodiments, the reservoir is separately maintained within the kit packaging in a manner to limit exposure of the reservoir to undesirable movement, friction, or other displacement that may otherwise occur during transportation of the kit (e.g., from a manufacturer). For example, because the reservoir can be in the form of a flexible bladder or membrane, in some embodiments, a kit includes a protective shell disposed about at least a portion of the reservoir. The shell is configured to limit exertion of a compressive force on the reservoir that could otherwise cause premature release of the fluid contained therein. In another example, the kit can include a cushion disposed about at least a portion of the reservoir, or another component of the delivery system, to absorb a shock from an impact that may occur during transportation of the kit, e.g., from a manufacturer. In some embodiments, at least one of the shell or cushion is removable prior to placement of the reservoir within the housing (i.e., in its second configuration). In other embodiments, at least one of the shell or the cushion can remain disposed about at least a portion of the reservoir when the reservoir is placed in its second configuration.

Although the kit is described herein as including a housing with an actuator and a cartridge assembly with a reservoir, in some embodiments, a kit can include any combination of delivery system components described herein. For example, in some embodiments, a kit can also include at least one of a second actuator, a fluid communicator, and one or more transfer structures. In some embodiments, the kit can include the housing in an assembled configuration (e.g., with coupled base and cover members), or in an unassembled configuration (e.g., with uncoupled base and cover members). Additionally, a kit can include more than one of any delivery system component, including those components described herein. For example, in some embodiments, a kit can include two or more housings, two or more reservoirs, multiple actuators, and/or two or more cartridge assemblies.

While various embodiments of the invention have been described above, it should be understood that they have been presented by way of example only, and not limitation. Where methods and steps described above indicate certain events occurring in certain order, those of ordinary skill in the art having the benefit of this disclosure would recognize that the ordering of certain steps may be modified and that such modifications are in accordance with the variations of the invention. Additionally, certain of the steps may be performed concurrently in a parallel process when possible, as well as performed sequentially as described above. The embodiments have been particularly shown and described, but it will be understood that various changes in form and details may be made.

For example, although various embodiments have been described as having particular features and/or combinations of components, other embodiments are possible having any combination or sub-combination of any features and/or components from any of the embodiments described herein. The specific configurations of the various components can also be varied. For example, the size and specific shape of the various components can be different than the embodiments shown, while still providing the functions as described herein. For example, in some embodiments, the first transfer structure 516 can have a differently shaped cut-out 576 or be differently sized such that no cut-out is needed. In another example, although the electrochemical actuator 502 has been illustrated and described herein as being included in the cartridge assembly 532, in some embodiments, the electrochemical actuator can be included in a different portion of the delivery device 500. For example, the electrochemical actuator 502 can be coupled to the housing (e.g., to the cover member 538) independent of the cartridge assembly 532. As such, the cartridge assembly 532 can be reconfigured (e.g., with an opening in its housing 534) to permit the electrochemical actuator 502 to engage or otherwise exert its force upon at least one of the second transfer structure 530 or the fluid source 504 during actuation. In some embodiments, the second transfer structure 530 can similarly be included in a different portion of the delivery device 500, such as being coupled to the housing 526 independent of the cartridge assembly 532.

What is claimed is:

1. An apparatus, comprising:
   a reservoir for containing a fluid;
   a first actuator having a first configuration and a second configuration, the first actuator configured to exert a first force on the reservoir when the first actuator moves from its first configuration to its second configuration such that a first volume of fluid within the reservoir is communicated out of the fluid reservoir;
   a transfer structure disposed between the first actuator and the reservoir, the transfer structure having a surface configured to engage the reservoir such that the first force exerted by the first actuator is distributed by the transfer structure across a surface of the reservoir engaged by the transfer structure; and
   a second actuator including an electrochemical actuator having a first configuration and a second configuration, at least a portion of the second actuator configured to deflect such that the second actuator exerts a second force on the reservoir when the second actuator moves from its first configuration to its second configuration such that a second volume of fluid within the reservoir is communicated out of the fluid reservoir.

2. The apparatus of claim 1, wherein the surface of the reservoir is a first surface, the second actuator configured to exert the second force on a second surface of the reservoir, the second surface being different than the first surface.

3. The apparatus of claim 1, wherein the surface of the reservoir is a first surface and the transfer structure is a first transfer structure, further comprising:
   a second transfer structure disposed between the second actuator and the reservoir, the second transfer structure having a surface configured to engage the reservoir such that the first force exerted upon actuation of the first actuator is distributed across a second surface of the reservoir engaged by the second transfer structure.

4. The apparatus of claim 1, wherein the first actuator includes a spring configured to exert the first force.

5. The apparatus of claim 1, wherein the transfer structure is configured to activate a trigger associated with the second actuator when the first actuator moves from its first configuration to its second configuration.

6. The apparatus of claim 1, wherein the first actuator is configured to exert the first force in a first direction with respect to the reservoir upon movement of the first actuator towards its second configuration, the second actuator is configured to exert the second force in a second direction, different than the first direction, with respect to the reservoir when the second actuator moves towards its second configuration.

7. The apparatus of claim 1, further comprising:
   a housing, wherein the first actuator is at least partially disposed within a housing; and
   a cartridge assembly including at least one of the second actuator and the reservoir, the cartridge assembly configured to be received in an interior region defined by the housing, the cartridge assembly configured to displace the transfer structure when the cartridge assembly is loaded into the interior region of the housing such that at least one of the first actuator and the second actuator is moved to its first configuration.

8. An apparatus, comprising:
   a reservoir configured to contain a fluid;
   a fluid communicator configured to be in fluid communication with the reservoir;
   a first actuator including a mechanical actuator, the first actuator coupled to the reservoir and configured to exert a first force on the reservoir to urge fluid within the reservoir out of the reservoir through the fluid communicator; and
   a second actuator including an electrochemical actuator having an electrode configured to deflect when the electrochemical actuator is discharged, the second actuator coupled to the reservoir and configured to be moved from a first configuration to a second configuration by a volumetric expansion of the second actuator by an electrochemical reaction involving a material of the second actuator and to exert a second force on the reservoir to urge fluid within the reservoir out of the reservoir through the fluid communicator.

9. The apparatus of claim 8, wherein the second actuator includes a first electrochemical actuator and a second electrochemical actuator.

10. The apparatus of claim 8, wherein the first actuator is configured to exert the first force for a first time period, the second actuator is configured to exert the second force for a second time period after the first time period.

11. The apparatus of claim 10, wherein the first time period at least partially overlaps with the second time period.

12. The apparatus of claim 8, further comprising:
    a transfer structure disposed between the reservoir and the first actuator, the transfer structure configured to transmit the first force to the reservoir upon actuation of the first actuator.

13. The apparatus of claim 8, wherein the first actuator urges a first volume of fluid out of the fluid reservoir and the second actuator urges a second volume of fluid out of the fluid reservoir, and the first volume of fluid and the second volume of fluid are collectively substantially equal to a total volume of fluid contained in the reservoir.

14. The apparatus of claim 8, further comprising:
a first transfer structure disposed between first actuator and the reservoir, the first transfer structure configured to transmit the first force to the reservoir upon actuation of the first actuator; and
a second transfer structure disposed between the second actuator and the reservoir, the second transfer structure configured to transmit the second force to the reservoir.

15. A method for delivering a fluid, comprising:
actuating a first actuator including a mechanical actuator to exert a first force on a fluid reservoir for a first time period such that a first volume of fluid within the fluid reservoir is communicated out of the reservoir and through a fluid communicator; and
actuating a second actuator including an electrochemical actuator such that the second actuator is moved from a first configuration to a second configuration in which the second actuator deflects and exerts a second force on the fluid reservoir for a second time period after the first time period such that a second volume of fluid within the fluid reservoir is communicated out of the reservoir and through the fluid communicator.

16. The method of claim 15, wherein actuation of the first actuator exerts the first force on the fluid reservoir in a first direction, actuation of the second actuator exerts the second force on the fluid reservoir in a second direction different than the first direction.

17. The method of claim 15, wherein the first force is exerted by the first actuator onto a transfer structure configured to transmit the first force to the reservoir.

18. A kit, comprising:
a housing including a first actuator and a second actuator, the second actuator including an electrochemical actuator, the second actuator configured to be moved from a first configuration to a second configuration in which the second actuator is deflected; and
a reservoir configured to contain a fluid, the reservoir having a first configuration in which the reservoir is separate from the housing, the reservoir having a second configuration in which at least a portion of the reservoir is received in the housing, the first actuator configured to exert a first force on the reservoir when the reservoir is in its second configuration such that at a first volume of the fluid is communicated out of the reservoir, the second actuator configured to exert a second force on the reservoir when the second actuator is moved from its first configuration to its second configuration such that a second volume of fluid is communicated out of the reservoir.

19. The kit of claim 18, further comprising:
a cartridge assembly configured to be slidably inserted into an opening in the housing, the cartridge assembly including the reservoir.

20. The kit of claim 18, wherein the first actuator is configured to be placed in a pre-loaded position when the cartridge assembly is inserted into the opening of the housing.

21. The apparatus of claim 1, wherein the first actuator is configured to cause the first volume of fluid to be communicated out of the fluid reservoir at a first delivery rate and the second actuator is configured to cause the second volume of fluid to be communicated out of the fluid reservoir at a second delivery rate different than the first delivery rate.

22. The apparatus of claim 8, wherein the first actuator is configured to urge fluid out of the reservoir through the fluid communicator at a first delivery rate and the second actuator is configured to urge fluid out of the reservoir through the fluid communicator at a second delivery rate different than the first delivery rate.

23. An apparatus, comprising:
a reservoir configured to contain a fluid;
a fluid communicator configured to be in fluid communication with the reservoir;
a first actuator including a mechanical actuator, the first actuator coupled to the reservoir and configured to exert a first force on the reservoir for a first time period to urge fluid within the reservoir out of the reservoir through the fluid communicator; and
a second actuator including an electrochemical actuator, the second actuator coupled to the reservoir and configured to be moved from a first configuration to a second configuration by a volumetric expansion of the second actuator by an electrochemical reaction involving a material of the second actuator and to exert a second force on the reservoir for a second time period after the first time period to urge fluid within the reservoir out of the reservoir through the fluid communicator.

24. The apparatus of claim 23, wherein the electrochemical actuator includes an electrode configured to deflect when the electrochemical actuator is discharged, the deflection of the electrode being operative to exert the second force on the reservoir.

25. The apparatus of claim 23, wherein the second actuator includes a first electrochemical actuator and a second electrochemical actuator.

26. The apparatus of claim 23, wherein the first time period at least partially overlaps with the second time period.

27. The apparatus of claim 23, further comprising:
a transfer structure disposed between the reservoir and the first actuator, the transfer structure configured to transmit the first force to the reservoir upon actuation of the first actuator.

28. The apparatus of claim 23, wherein the first actuator urges a first volume of fluid out of the fluid reservoir and the second actuator urges a second volume of fluid out of the fluid reservoir, and the first volume of fluid and the second volume of fluid are collectively substantially equal to a total volume of fluid contained in the reservoir.

29. The apparatus of claim 23, wherein the first actuator is configured to urge fluid out of the reservoir through the fluid communicator at a first delivery rate and the second actuator is configured to urge fluid out of the reservoir through the fluid communicator at a second delivery rate different than the first delivery rate.

* * * * *